US012624042B2

(12) United States Patent
Shu et al.

(10) Patent No.: US 12,624,042 B2
(45) Date of Patent: May 12, 2026

(54) COMPOUND FOR TARGETED DEGRADATION OF BTK AND ANTI-TUMOUR USE THEREOF

(71) Applicant: SHANGHAI MEIZER PHARMACEUTICALS CO., LTD., Shanghai (CN)

(72) Inventors: Yongzhi Shu, Shanghai (CN); Fengjun Luo, Shanghai (CN)

(73) Assignee: SHANGHAI MEIZER PHARMACEUTICALS CO., LTD., Shanghai (CN)

( * ) Notice: Subject to any disclaimer, the term of this patent is extended or adjusted under 35 U.S.C. 154(b) by 406 days.

(21) Appl. No.: 18/250,477

(22) PCT Filed: Oct. 26, 2021

(86) PCT No.: PCT/CN2021/126315

§ 371 (c)(1),
(2) Date: Apr. 25, 2023

(87) PCT Pub. No.: WO2022/089400

PCT Pub. Date: May 5, 2022

(65) Prior Publication Data

US 2024/0002389 A1 Jan. 4, 2024

(30) Foreign Application Priority Data

Oct. 26, 2020 (CN) ........................ 202011160099.3

(51) Int. Cl.

| | |
|---|---|
| ***C07D 487/04*** | (2006.01) |
| ***A61K 31/519*** | (2006.01) |
| ***A61P 35/00*** | (2006.01) |

(52) U.S. Cl.
CPC ........... *C07D 487/04* (2013.01); *A61P 35/00* (2018.01)

(58) Field of Classification Search
CPC ..... C07D 487/04; A61K 31/519; A61P 35/02; C12Q 1/001
USPC ........................................ 544/262; 514/262.1
See application file for complete search history.

(56) References Cited

FOREIGN PATENT DOCUMENTS

| | | | |
|---|---|---|---|
| CN | 109422751 | A | 3/2019 |
| CN | 109422752 | A | 3/2019 |
| CN | 109422753 | A | 3/2019 |
| CN | 109963844 | A | 7/2019 |
| CN | 111662294 | A | 9/2020 |
| WO | 2017117473 | A1 | 7/2017 |
| WO | 2018098288 | A1 | 5/2018 |
| WO | 2019127008 | A1 | 7/2019 |
| WO | 2019148150 | A1 | 8/2019 |
| WO | 2019177902 | A1 | 9/2019 |

OTHER PUBLICATIONS

International Search Report (with English translation) and Written Opinion issued in PCT/CN2021/126315, dated Dec. 22, 2021, 13 pages provided.

Saul Jaime-Figueroa et al., "Design, synthesis and biological evaluation of Proteolysis Targeting Chimeras (PROTACs) as a BTK degraders with improved pharmacokinetic properties", Bioorganic & Medicinal Chemistry Letters, vol. 30, No. 3, Dec. 13, 2019, abstract, p. 3, left column, line 15 to p. 4, right column, line 6, and p. 7, compound SJF620.

*Primary Examiner* — Charanjit Aulakh
(74) *Attorney, Agent, or Firm* — HSML P.C.

(57) ABSTRACT

Provided in the present invention are a compound for the targeted degradation of BTK and the anti-tumor use thereof. In particular, in the present invention, a series of compounds are prepared and screened, the inhibitory and degradation activities of said compounds against Bruton's tyrosine kinase (BTK) are verified, and finally a compound with good druggability is found. The compound can be used for treating diseases associated with the activity or the expression quantity of Bruton's tyrosine kinase (BTK).

7 Claims, No Drawings

COMPOUND FOR TARGETED DEGRADATION OF BTK AND ANTI-TUMOUR USE THEREOF

TECHNICAL FIELD

The present invention belongs to the field of medicine, and in particular relates to a compound for targeted degradation of Btk and anti-tumour use thereof.

BACKGROUND

Btk, i.e. Bruton's tyrosine kinase, is a member of the Tec family of non-receptor tyrosine kinases. It is an essential gene for cell differentiation and proliferation, and is expressed in B-cell lymphoma, acute lymphoblastic leukemia (ALL) and plasmacytoma. Btk is a key component of the B cell receptor (BCR) signaling pathway and is a good site for targeted treatment of diseases such as B-cell lymphoma.

Btk is a key regulator of B cell development, activation, signal transduction and survival, and is involved in the regulation of angiogenesis, cell proliferation and apoptosis, and cell motility. In addition, Btk is also involved in many other hematopoietic cell signaling pathways, for example, in the signaling pathway mediated by Toll-like receptors and cytokine receptors in macrophages, and in the signal transduction of IgE receptors in mast cells, etc.

Recent studies have shown that Btk signaling pathway is a new hotspot currently in clinical treatment research for non-Hodgkin's lymphoma (NHL), especially chronic lymphocytic leukemia (CLL), B-cell lymphoma and autoimmune diseases (rheumatoid arthritis, psoriasis, etc.)

Therefore, those skilled in the art are committed to developing compounds that can effectively inhibit and degrade Btk.

SUMMARY OF THE INVENTION

The object of the present invention is to provide a compound with good permeability for inhibiting and degrading Btk, and its application.

In the first aspect of the present invention, there is provided a compound as follows, or a pharmaceutically acceptable salt thereof, or a solvate thereof, or a deuterated compound thereof:

| NO. | Structure |
|---|---|
| 1 | 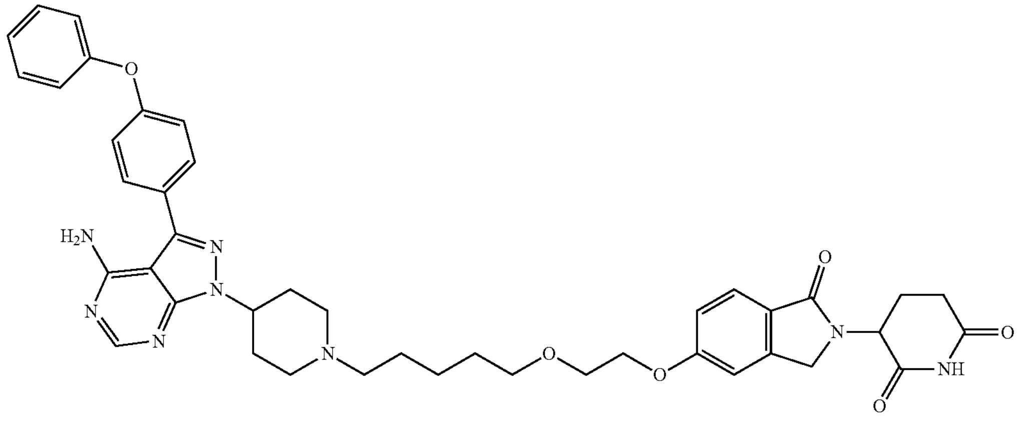 [SMILES: Nc1ncnc2c1c(-c1ccc(Oc3ccccc3)cc1)nn2C1CCN(CCCCCOCCOc2ccc3c(c2)CN(C2CCC(=O)NC2=O)C3=O)CC1] |
| 2 | 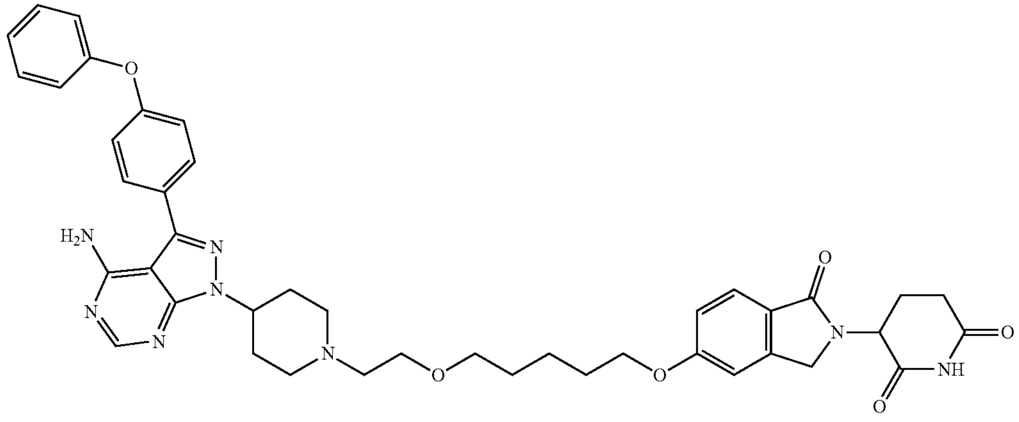 [SMILES: Nc1ncnc2c1c(-c1ccc(Oc3ccccc3)cc1)nn2C1CCN(CCOCCCCCOc2ccc3c(c2)CN(C2CCC(=O)NC2=O)C3=O)CC1] |

-continued

| NO. | Structure |
| --- | --- |
| 3 | 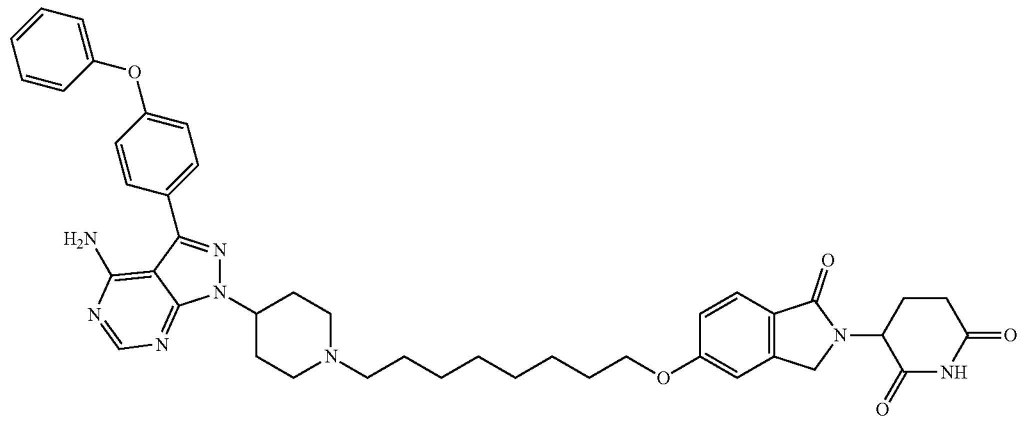 [SMILES: Nc1ncnc2c1c(-c1ccc(Oc3ccccc3)cc1)nn2C1CCN(CCCCCCCCOc2ccc3c(c2)CN(C2CCC(=O)NC2=O)C3=O)CC1] |

In the second aspect of the present invention, there is provided a pharmaceutical composition, which comprises the compound according to the first aspect or an isomer thereof, a prodrug thereof, a pharmaceutically acceptable salt thereof, and a pharmaceutically acceptable carrier.

In another preferred example, the pharmaceutical composition further comprises one or more antitumor agents.

In another preferred example, the pharmaceutical composition is used for inhibiting the activity of Bruton's tyrosine protein kinase (Btk) or reducing the level of Bruton's tyrosine protein kinase (Btk).

In another preferred example, the pharmaceutical composition is used for treating diseases related to the activity or expression level of Bruton's tyrosine kinase (Btk).

In the third aspect of the present invention, there is provided a use of the compound according to the first aspect of the present invention for:

(a) preparation of drugs for the treatment of diseases related to the activity or expression level of Bruton's tyrosine kinase (Btk);
(b) preparation of Bruton's tyrosine kinase (Btk) targeting inhibitors or degradation agents;
(c) non-therapeutic inhibition or degradation of the activity of Bruton's tyrosine kinase (Btk) in vitro;
(d) non-therapeutic inhibition of tumor cell proliferation in vitro; and/or
(e) treatment of diseases related to the activity or expression level of Bruton's tyrosine kinase (Btk).

In another preferred example, the diseases include tumors and autoimmune diseases; preferably, the tumors include non-Hodgkin's lymphoma (NHL), chronic lymphocytic leukemia (CLL), B-cell lymphoma, etc.; the autoimmune diseases include rheumatoid arthritis, psoriasis, etc.

DETAILED DESCRIPTION OF THE INVENTION

After extensive and intensive research, the present inventors have prepared and screened a series of compounds, and verified the inhibitory and degradation activities of these compounds on Bruton's tyrosine protein kinase (Btk). Although these compounds all showed Btk inhibitory and degradation activities, the research found that the activities of different compounds were quite different, and the membrane permeability test of each compound unexpectedly found a compound with excellent permeability. Compared with other similar compounds, it has achieved unexpected excellent technical effects, and thus has good druggability. So it can be used to treat diseases related to the activity or expression of Bruton's tyrosine protein kinase (Btk), such as tumors. The present invention has been completed on this basis.

Term

In the present invention, the term "containing", "comprising" or "including" means that various ingredients can be used together in the mixture or composition of the present invention. Thus, the terms "consisting essentially of" and "consisting of" are included in the term "containing".

In the present invention, the term "pharmaceutically acceptable" ingredient refers to a substance suitable for human and/or animals without excessive adverse side effects (such as toxicity, irritation and allergy), that is, with a reasonable benefit/risk ratio.

In the present invention, the term "effective amount" refers to an amount of a therapeutic agent to treat, alleviate or prevent a target disease or condition, or an amount that exhibits a detectable therapeutic or preventive effect. The exact effective amount for a subject will depend on the subject's size and health, the nature and extent of the condition, and the therapeutic agent and/or combination of therapeutic agents chosen for administration. Therefore, it is not useful to specify an accurate effective amount in advance. However, for a given condition, routine experimentation can be used to determine the effective amount, which the clinician can determine.

Unless otherwise specified, all compounds present in the present invention are intended to include all possible optical isomers, such as a single chiral compound, or a mixture of various chiral compounds (i.e., a racemate). Among all the compounds of the present invention, each chiral carbon atom may optionally be in the R configuration or the S configuration, or a mixture of the R configuration and the S configuration.

As used herein, the term "compound of the present invention" refers to each compound shown herein. The term also includes the various crystalline forms, pharmaceutically acceptable salts, hydrates or solvent compounds of each compound.

As used herein, the term "pharmaceutically acceptable salt" refers to a salt of the compound of the present invention with an acid or base suitable for use as a medicament. The pharmaceutically acceptable salts include inorganic and organic salts. One preferred class of salts is salts of the compound of the present invention with an acid. Suitable acids for forming salts include, but are not limited to, inorganic acids such as hydrochloric acid, hydrobromic acid, hydrofluoric acid, sulfuric acid, nitric acid, phosphoric acid, etc., organic acids such as formic acid, acetic acid, propionic acid, oxalic acid, malonic acid, succinic acid, fumaric acid, maleic acid, lactic acid, malic acid, tartaric acid, citric acid, picric acid, methanesulfonic acid, benzylsulfonic acid, benzenesulfonic acid etc.; and acidic amino acids such as aspartic acid, glutamic acid etc.

Compounds and Pharmaceutically Acceptable Salts Thereof

The present invention relates to the following compounds or pharmaceutically acceptable salts or deuterated compounds thereof:

| No. | Structure |
| --- | --- |
| 1 | 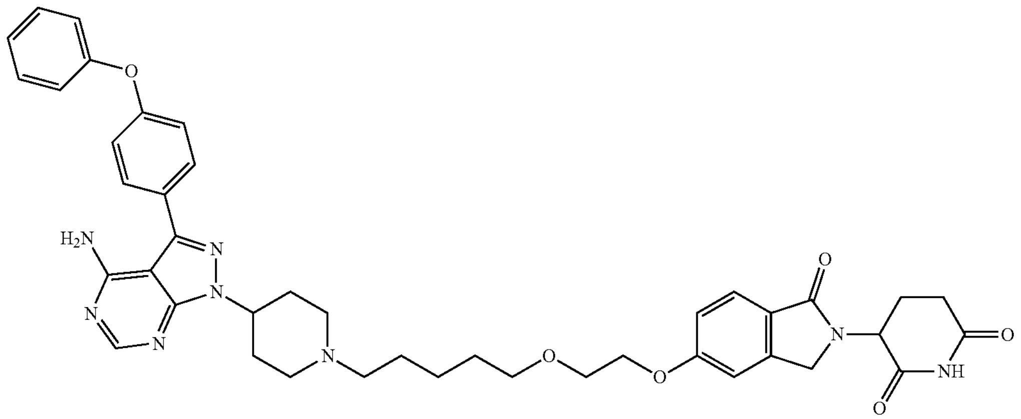 [SMILES: Nc1ncnc2c1c(-c1ccc(Oc3ccccc3)cc1)nn2C1CCN(CCCCCOCCOc2ccc3c(c2)CN(C2CCC(=O)NC2=O)C3=O)CC1] |
| 2 | 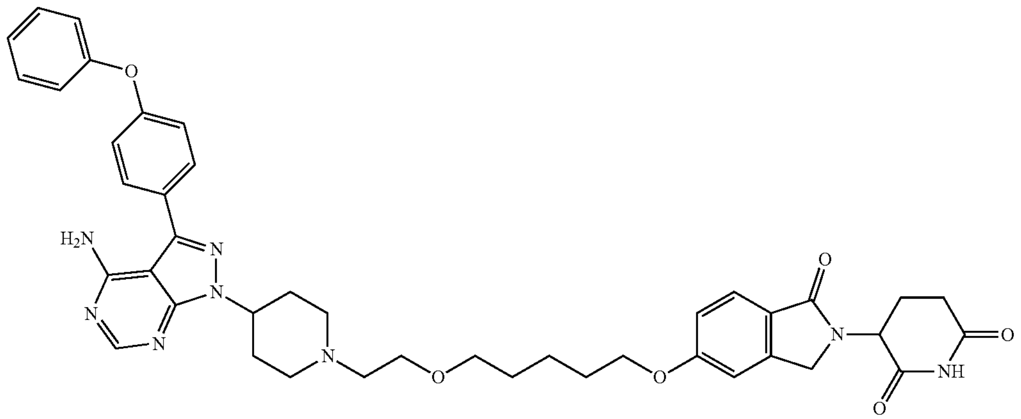 [SMILES: Nc1ncnc2c1c(-c1ccc(Oc3ccccc3)cc1)nn2C1CCN(CCOCCCCCOc2ccc3c(c2)CN(C2CCC(=O)NC2=O)C3=O)CC1] |
| 3 | 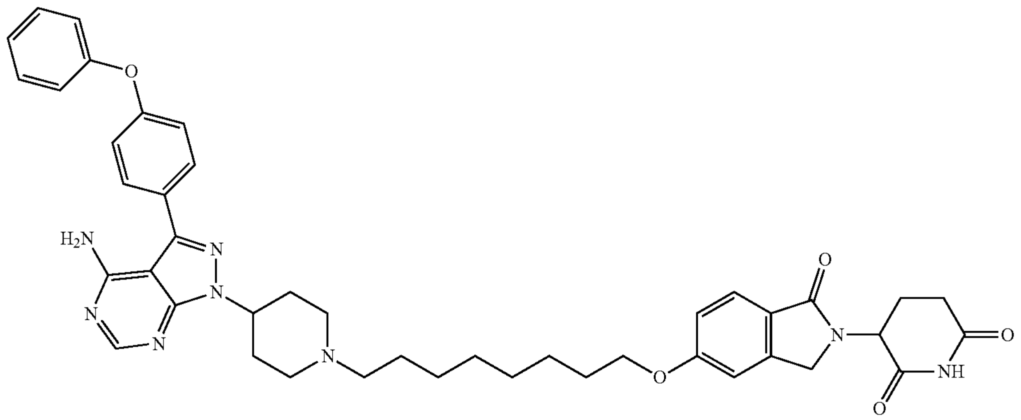 [SMILES: Nc1ncnc2c1c(-c1ccc(Oc3ccccc3)cc1)nn2C1CCN(CCCCCCCCOc2ccc3c(c2)CN(C2CCC(=O)NC2=O)C3=O)CC1] |

Through a lot of research, the present invention has carried out a lot of optimization and screening on the structure of the compound that inhibits and degrades Btk. The results show that the above compound, compared with other compounds, has shown excellent permeability, low efflux ratio, and has good druggability; moreover, it shows significant inhibitory effect on ibrutinib-resistant tumor cells, and has stronger anti-tumor activity. Unexpected technical effects have been achieved.

The compound of the present invention may form a pharmaceutically acceptable salt with an inorganic acid, an organic acid or a base. The inorganic acid includes, but is not limited to, hydrochloric acid, hydrobromic acid, nitric acid, perchloric acid, sulfuric acid, or phosphoric acid; the organic acid includes, but is not limited to, methanesulfonic acid, trifluoromethanesulfonic acid, ethanesulfonic acid, benzenesulfonic acid, p-toluenesulfonic acid, fumaric acid, oxalic acid, acetic acid, maleic acid, ascorbic acid, lactic acid, tartaric acid, malonic acid, glycolic acid, succinic acid, and propionic acid; the bases include, but are not limited to, inorganic salts and amines.

The term of a pharmaceutically acceptable salt refers to those salts which, according to medical judgment, are suitable for use in contact with human and mammalian tissues without excessive toxicity, irritation, allergic reactions, and the like. Pharmaceutically acceptable salts are well known in the art.

Application

The compounds of the present invention can be used for one or more of the following purposes:

(a) preparation of drugs for the treatment of diseases related to the activity or expression level of Bruton's tyrosine kinase (Btk);

(b) preparation of Bruton's tyrosine kinase (Btk) targeting inhibitors or degradation agents;

(c) non-therapeutic inhibition or degradation of the activity of Bruton's tyrosine kinase (Btk) in vitro;

(d) non-therapeutic inhibition of tumor cell proliferation in vitro; and/or (e) treatment of diseases related to the activity or expression level of Bruton's tyrosine kinase (Btk).

In another preferred example, the diseases include tumors and autoimmune diseases; preferably, the tumors include non-Hodgkin's lymphoma (NHL), chronic lymphocytic leukemia (CLL), B-cell lymphoma, etc.; the autoimmune diseases include rheumatoid arthritis, psoriasis, etc.

The compound of the present invention can be used to prepare a kind of pharmaceutical composition, and the pharmaceutical composition comprises: (i) an effective dose compound of the present invention, or its pharmaceutically acceptable salt; and (ii) a pharmaceutically acceptable carrier.

In another preferred example, the effective amount refers to a therapeutically effective amount or an inhibitory effective amount.

In another preferred example, when an inhibitory effective amount of the compound of the present invention or a pharmaceutically acceptable salt thereof is administered to the inhibited subject, the inhibitory effective amount is 0.001-500 nmol/L, preferably 0.01-200 nmol/L.

In particular, the present invention also provides a method for treating diseases related to the activity or expression of Bruton's tyrosine protein kinase (Btk), the method comprising: administering a therapeutically effective amount of the compound of the present invention to the subject, or the pharmaceutical composition containing the compound of the present invention as an active ingredient.

Pharmaceutical Composition and Administration

Since the compound of the present invention has excellent inhibitory activity on Bruton's tyrosine kinase (Btk), the compound of the present invention and its various crystal forms, pharmaceutically acceptable inorganic or organic salts, hydrates or solvates and the pharmaceutical composition containing the compound of the present invention as a main active ingredient can be used for treating, preventing, and alleviating diseases related to Btk activity or expression level. According to the prior art, the compounds of the present invention are useful for treating diseases including tumors and the like.

The pharmaceutical composition of the present invention comprises the compound of the present invention or the pharmaceutically acceptable salts thereof in a safe and effective dosage range and pharmaceutically acceptable excipients or carriers. The "safe and effective amount" means the amount of the compound is sufficient to significantly improve the condition, but will not have serious side effects. Generally, the pharmaceutical composition contains 1-2000 mg of the compound of the present invention per dose, preferably, 5-500 mg of the compound of the present invention per dose. Preferably, "one dose" is a capsule or tablet.

"Pharmaceutically acceptable carrier" means one or more compatible solid or liquid fillers or gelatinous materials which are suitable for human use and should be of sufficient purity and sufficiently low toxicity. "Compatible" herein means that each component in the composition and a compound of the present invention can be well blended with each other between them, without significantly reducing the efficacy of the compounds. Some examples of pharmaceutically acceptable carriers include cellulose and the derivatives thereof (such as sodium carboxymethyl cellulose, sodium ethyl cellulose, cellulose acetate, etc.), gelatin, talc, solid lubricants (such as stearic acid, magnesium stearate), calcium sulfate, vegetable oils (such as soybean oil, sesame oil, peanut oil, olive oil, etc.), polyols (such as propylene glycol, glycerol, mannitol, sorbitol, etc.), emulsifiers (such as Tween®), wetting agent (such as sodium dodecyl sulfate), coloring agents, flavoring agents, stabilizers, antioxidants, preservatives, pyrogen-free water, etc.

There is no special limitation of administration mode for the compound or pharmaceutical compositions of the present invention, and the representative administration mode includes (but is not limited to): oral, intratumoral, rectal, parenteral (intravenous, intramuscular or subcutaneous), and topical administration.

Solid dosage forms for oral administration include capsules, tablets, pills, powders and granules. In these solid dosage forms, the active compounds are mixed with at least one conventional inert excipient (or carrier), such as sodium citrate or dicalcium phosphate, or mixed with any of the following components: (a) fillers or compatibilizer, for example, starch, lactose, sucrose, glucose, mannitol and silicic acid; (b) binders, for example, hydroxymethyl cellulose, alginates, gelatin, polyvinylpyrrolidone, sucrose and arabic gum; (c) humectant, such as, glycerol; (d) disintegrating agents such as agar, calcium carbonate, potato starch or tapioca starch, alginic acid, certain composite silicates, and sodium carbonate; (e) dissolution-retarding agents, such as paraffin; (f) absorption accelerators, for example, quaternary ammonium compounds; (g) wetting agents, such as cetyl alcohol and glyceryl monostearate; (h) adsorbents, for example, kaolin; and (i) lubricants such as talc, stearin calcium, magnesium stearate, solid polyethylene glycol, sodium lauryl sulfate, or the mixtures thereof. In capsules, tablets and pills, the dosage forms may also contain buffering agents.

The solid dosage forms such as tablets, sugar pills, capsules, pills and granules can be prepared by using coating and shell materials, such as enteric coatings and any other materials known in the art. They can contain an opaque agent and the release of the active compounds or compounds in the compositions can be released in a delayed mode in a given portion of the digestive tract. Examples of the embedding components include polymers and waxes. If necessary, the active compounds and one or more above excipients can form microcapsules.

Liquid dosage forms for oral administration include pharmaceutically acceptable emulsions, solutions, suspensions, syrups or tinctures. In addition to the active compounds, the liquid dosage forms may contain any conventional inert diluents known in the art such as water or other solvents, solubilizers and emulsifiers, for example, ethanol, isopropanol, ethyl carbonate, ethyl acetate, propylene glycol, 1,3-butanediol, dimethyl formamide, as well as oil, in particular, cottonseed oil, peanut oil, corn germ oil, olive oil, castor oil and sesame oil, or the combination thereof.

Besides these inert diluents, the composition may also contain additives such as wetting agents, emulsifiers and suspending agent, sweetener, flavoring agents and perfume.

In addition to the active compounds, the suspension may contain suspending agent, for example, ethoxylated isooctadecanol, polyoxyethylene sorbitol and sorbitan esters, microcrystalline cellulose, methanol aluminum and agar, or the combination thereof.

The compositions for parenteral injection may comprise physiologically acceptable sterile aqueous or anhydrous solutions, dispersions, suspensions or emulsions, and sterile powders which can be re-dissolved into sterile injectable solutions or dispersions. Suitable aqueous and non-aqueous carriers, diluents, solvents or excipients include water, ethanol, polyols and any suitable mixtures thereof.

The dosage forms for topical administration of compounds of the present invention include ointments, powders, patches, aerosol, and inhalants. The active ingredients are mixed with physiologically acceptable carriers and any preservatives, buffers, or propellant if necessary, under sterile conditions.

Compounds of the present invention can be administrated alone, or in combination with any other pharmaceutically acceptable compounds.

When the pharmaceutical compositions are used, a safe and effective amount of compound of the present invention is applied to a mammal (such as human) in need of, in which the dose of administration is a pharmaceutically effective dose. For a person weighed kg, the daily dose is usually 1-2000 mg, preferably 5-500 mg. Of course, the particular dose should also depend on various factors, such as the route of administration, the healthy condition of patient, which are well within the skills of an experienced physician.

The Main Advantages of the Present Invention Include:

1. The compound of the present invention has good permeability, acts as a non-p-glycoprotein transport substrate, has no efflux phenomenon, has good druggability, and has achieved unexpected excellent technical effects.
2. The compound of the present invention can degrade the activity of Btk at very low concentration.
3. The present invention provides a class of pharmaceutical compositions for treating diseases related to Btk enzyme activity.
4. The compound of the present invention not only has significant degradative activity to wild-type BTK, but also shows excellent degradative activity to BTK-C481S mutant protein.

The present invention will be further illustrated below with reference to the specific examples. It should be understood that these examples are only to illustrate the invention but not to limit the disclosure of the invention. The experimental methods without specific conditions in the following embodiments are generally carried out according to conventional conditions, or in accordance with the conditions recommended by the manufacturer. Unless stated otherwise, percentages and parts are percentages by weight and parts by weight. The biological materials (such as cell lines and antibodies) involved in the present invention can be purchased through commercial channels.

Example 1 Synthesis of Compound 1

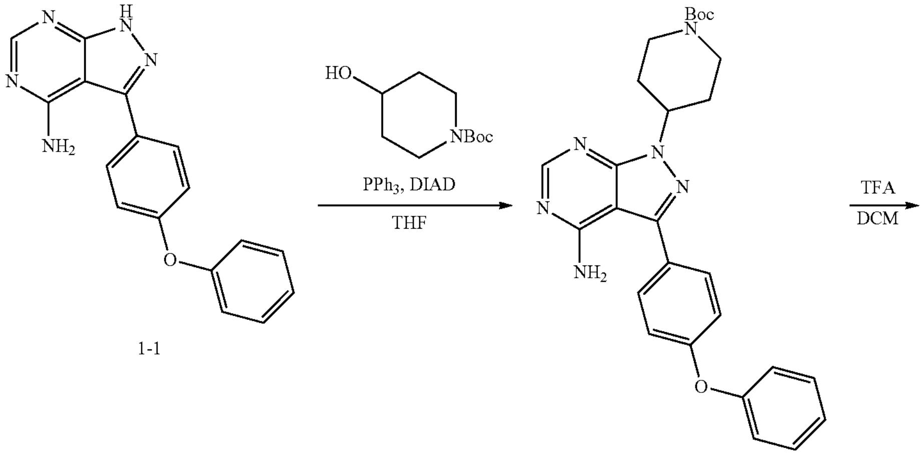

1-1
1-2

-continued
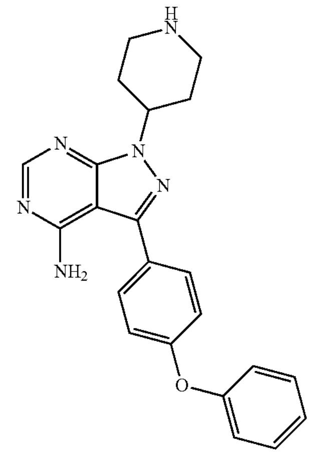
1-3
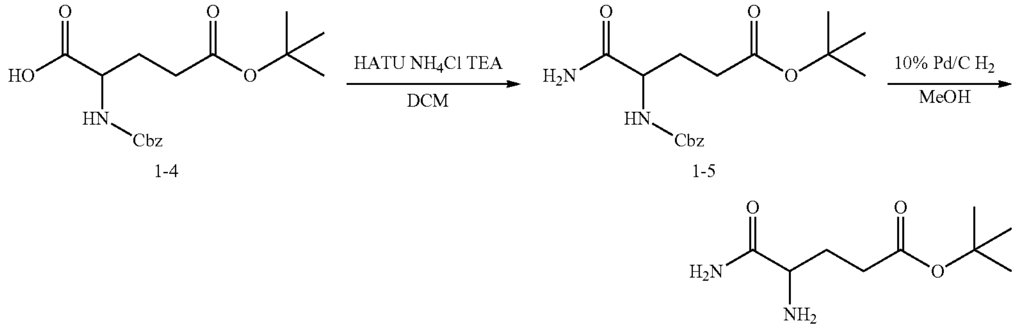
1-4 1-5 1-6
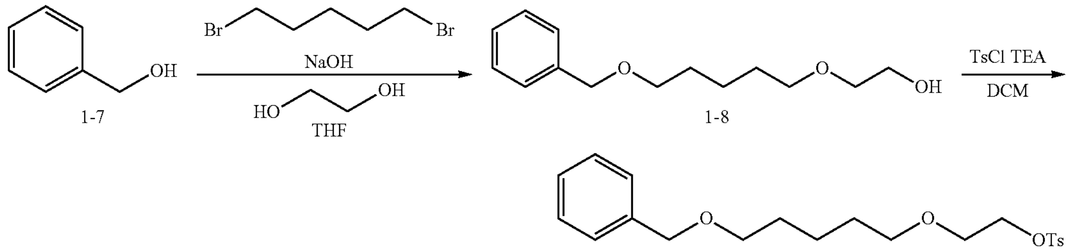
1-7 1-8 1-9
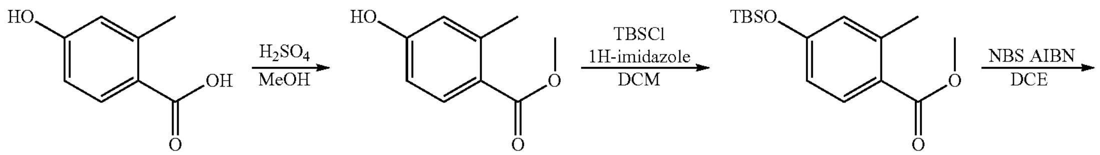
1-10 1-11 1-12
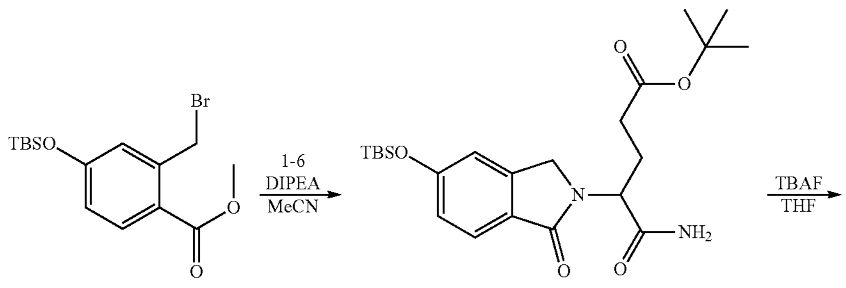
1-13 1-14

-continued
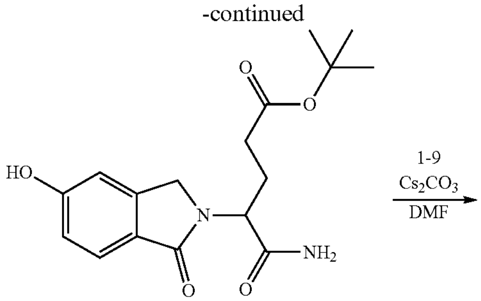
1-15
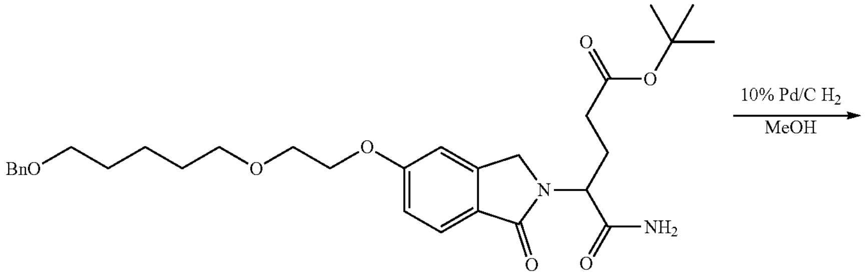
1-16
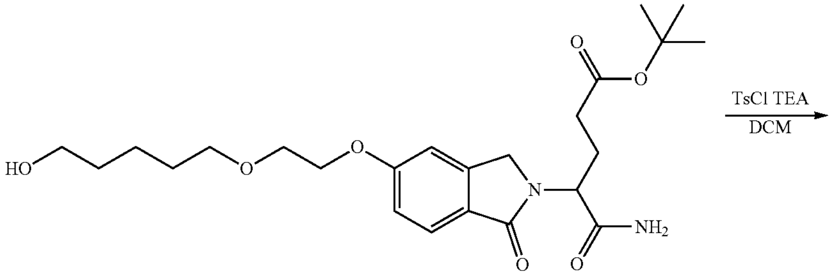
1-17
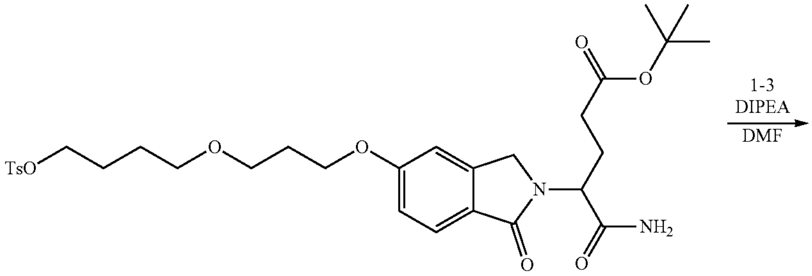
1-18
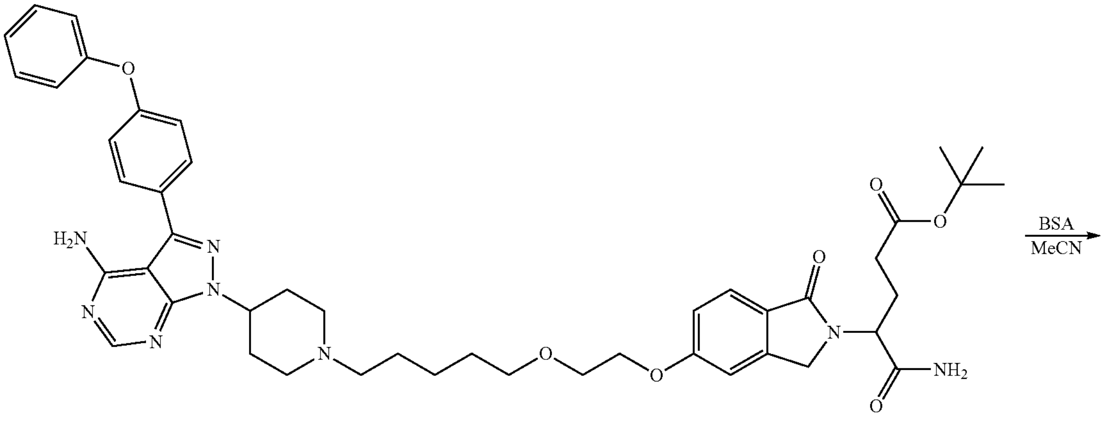
1-19

-continued

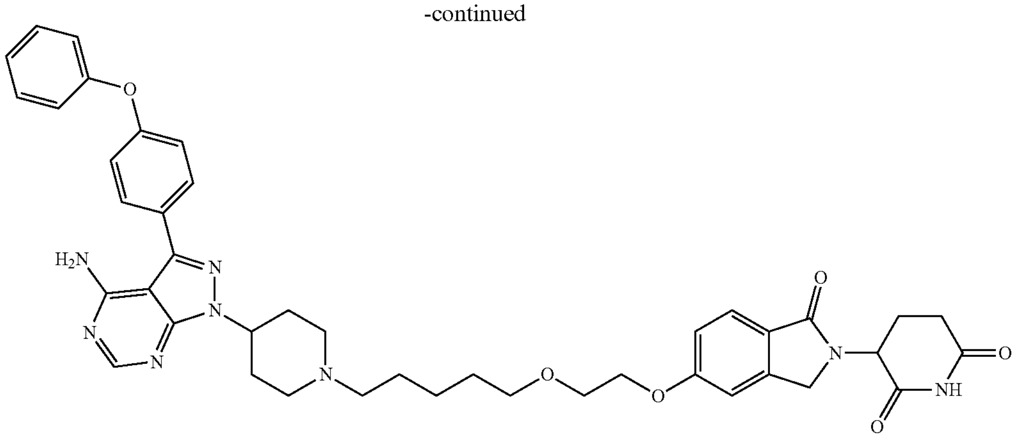

1

1. Synthesis of Compound 1-2

Compound 1-1 (3.0 g, 10 mmol), N-Boc-4-hydroxypiperidine (2.4 g, 12 mmol) and triphenylphosphine (3.9 g, 15 mmol) were dissolved in tetrahydrofuran (50 mL), and diisopropyl azodicarboxylate (3.0 g, 15 mmol) was added dropwise, and the mixture was reacted at room temperature under nitrogen atmosphere for 16 hours. The reaction solution was diluted with an appropriate amount of ethyl acetate, washed with saturated saline solution, concentrated and evaporated to dryness, and purified by silica gel column chromatography (dichloromethane:methanol=50:1 elution) to obtain 3.0 g of a brownish-red foamy product with a yield of 78%.

LC-MS: 487.4 $(M+H)^+$.

2. Synthesis of Compound 1-3

Compound 1-2 (3.0 g, 6 mmol) was dissolved in dichloromethane (30 mL), trifluoroacetic acid (3 mL) was slowly added dropwise, and the mixture was reacted at room temperature for 24 hours. The reaction solution was concentrated and evaporated to dryness, and purified by silica gel column chromatography (dichloromethane:methanol=30:1 elution) to obtain 2.2 g of a white foamy product with a yield of 93%.

LC-MS: 387.3 $(M+H)^+$.

$^1$H NMR (400 MHz, DMSO-d6) δ 8.26 (s, 1H), 7.66 (d, J=8.0 Hz, 2H), 7.44 (t, J=7.6 Hz, 2H), 7.31-7.04 (m, 5H), 4.98 (prs, 1H), 3.40-3.33 (m, 2H), 3.13-2.99 (m, 2H), 2.36-2.18 (m, 2H), 2.13-1.96 (m, 2H).

3. Synthesis of Compound 1-5

Compound 1-4 (50.0 g, 148 mmol) and ammonium chloride (39.3 g, 742 mmol) were dissolved in dichloromethane (700 mL), and N,N,N,N-tetramethyl-O-(7-azabenzotriazol-1-yl) urea hexafluorophosphate (68.0 g, 180 mmol) and triethylamine (100 mL, 0.75 mmol) were added, and the mixture was react at room temperature for 16 hours. The reaction solution was washed successively with dilute hydrochloric acid and saturated saline solution, the organic phase was concentrated and evaporated to dryness, and purified by silica gel column chromatography (dichloromethane:methanol=80:1) to obtain 21.4 g of white solid product with a yield of 43%.

LC-MS: 359.2 $(M+H)^+$.

4. Synthesis of Compound 1-6

Compound 1-5 (21.4 g, 64 mmol) was dissolved in methanol (500 mL), 10% palladium-carbon (3.0 g wet weight) was added, and the mixture was reacted at room temperature under hydrogen atmosphere for 24 hours. The reaction solution was filtered, concentrated and evaporated to dryness to obtain 11.7 g of a light yellow oily product with a yield of 91%.

LC-MS: 203.1 $(M+H)^+$.

Synthesis of Compound 1-8

Compounds 1-7 (10.8 g, 100 mmol) and 1,5-dibromopentane (22.8 g, 100 mmol) were dissolved in tetrahydrofuran solution (500 mL), and sodium hydroxide (12.0 g, 300 mmol) was added in batches, the mixture was reacted at reflux for 16 hours. Ethylene glycol (12.4 g, 200 mmol) and sodium hydroxide (12.0 g, 300 mmol) were added to the system, and the mixture was reacted at refluxed for 16 hours. The reaction solution was cooled, slowly poured into ice water, and extracted with ethyl acetate. The extract was washed with saturated saline solution, concentrated and evaporated to dryness, and purified by silica gel column chromatography(petroleum ether:ethyl acetate=5:1 elution) to obtain 5 g of a light yellow oily liquid product with a yield of 21%.

LC-MS: 239.4 $(M+H)^+$.

6. Synthesis of Compound 1-9

Compound 1-8 (4 g, 16.8 mmol) and p-toluenesulfonyl chloride (3.8 g, 20.1 mmol) were dissolved in dichloromethane (150 mL), triethylamine (4.7 mL, 33.6 mmol) was added, and the mixture was reacted at room temperature for 16 hours. The reaction solution was slowly poured into water and extracted with dichloromethane. The extract was washed with saturated saline solution, concentrated and evaporated to dryness, and purified by silica gel column chromatography (petroleum ether:ethyl acetate=80:1 elution) to obtain 3.0 g of a colorless oily product with a yield of 46%.

LC-MS: 393.3 $(M+H)^+$.

7. Synthesis of Compound 1-11

Compound 1-10 (25.0 g, 164 mmol) was dissolved in methanol solution (150 mL), sulfuric acid (5 mL) was slowly added dropwise under ice bath, and the mixture was reacted at reflux for 3 hours. The reaction solution was concentrated, slowly poured into water, and extracted with ethyl acetate. The extract was washed with saturated saline solution, concentrated and evaporated to dryness to obtain 20.5 g of a light red solid product with a yield of 75%.

LC-MS: 167.1 $(M+H)^+$.

$^1$H NMR (400 MHz, DMSO-d6) δ 10.15 (s, 1H), 7.77 (d, J=9.2 Hz, 1H), 6.72-6.65 (m, 2H), 3.76 (s, 3H), 2.47 (s, 3H).

8. Synthesis of Compound 1-12

Compound 1-11 (20.0 g, 120 mmol) and imidazole (12.2 g, 180 mmol) were dissolved in dichloromethane (200 mL), tert-butyldimethylsilyl chloride (21.6 g, 144 mmol) was added, and the mixture was reacted at room temperature for 16 hours. The reaction solution was filtered, concentrated and evaporated to dryness, and purified by silica gel column chromatography (petroleum ether:ethyl acetate=50:1 elution) to obtain 19.8 g of a colorless oily product with a yield of 59%.

LC-MS: 281.2 $(M+H)^+$.

9. Synthesis of Compound 1-13

Compound 1-12 (19.8 g, 70 mmol) and N-bromosuccinimide (13.8 g, 78 mmol) were dissolved in dichloroethane (200 mL), and azobisisobutyronitrile (1.1 g, 7 mmol) was added, and the mixture was reacted at 90° C. for 16 hours. The reaction solution was concentrated and purified by silica gel column chromatography (petroleum ether:ethyl acetate=100:1) to obtain 30.1 g of a colorless oily product (purity 40%, containing a large amount of raw material and dibromide, difficult to separate).

LC-MS: 381.1 $(M+Na)^+$.

10. Synthesis of Compound 1-14

Compounds 1-13 (24.0 g, 26.8 mmol, 40%) and 1-6 (6.8 g, 33.6 mmol) were dissolved in acetonitrile (200 mL), and N,N-diisopropylethylamine (12 mL, 68 mmol) was added, and the mixture was reacted at reflux for 16 hours. The reaction solution was concentrated and purified by silica gel column chromatography (petroleum ether:ethyl acetate=1:1 elution) to obtain 6.0 g of a brownish-yellow oily product with a yield of 40%.

LC-MS: 449.3 $(M+H)^+$.

11. Synthesis of Compound 1-15

Compound 1-14 (6.0 g, 13.2 mmol) was dissolved in methanol (100 mL), tetrabutylammonium fluoride (6.8 g, 26.4 mmol) was added, and the mixture was reacted at room temperature for 16 hours. The reaction solution was concentrated and purified by silica gel column chromatography (dichloromethane:methanol=20:1 elution) to obtain 3.7 g of a brown oily product with a yield of 83%.

LC-MS: 335.3 $(M+H)^+$.

$^1$H NMR (400 MHz, DMSO-d6) δ 10.13 (s, 1H), 7.58-7.42 (m, 2H), 7.16 (s, 1H), 6.94 (d, J=2.0 Hz, 1H), 6.86 (dd, J=8.4, 2.0 Hz, 1H), 4.72-4.63 (m, 1H), 4.55-4.29 (m, 2H), 2.21-2.06 (m, 3H), 2.02-1.89 (m, 1H), 1.33 (s, 9H).

12. Synthesis of Compound 1-16

Compound 1-15 (800 mg, 2.4 mmol) and cesium carbonate (1.5 g, 4.8 mmol) were dissolved in N,N-dimethylformamide (10 mL), and 1-9 (1.9 g, 4.8 mol) was added, and the mixture was reacted at 50° C. for 24 hours. The reaction solution was slowly poured into water, extracted with ethyl acetate, the extract was washed with saturated saline solution, concentrated and evaporated to dryness, and purified by silica gel column chromatography (dichloromethane:methanol=50:1 elution) to obtain 504 mg of a brown-yellow foamy product with a yield of 38%.

LC-MS: 555.5 $(M+H)^+$.

13. Synthesis of Compound 1-17

Compound 1-16 (500 mg, 0.9 mmol) was dissolved in methanol (30 mL), 10% palladium-carbon (50 mg wet weight) was added, and the mixture was reacted at room temperature under hydrogen atmosphere for 16 hours. The reaction solution was filtered, concentrated and evaporated to dryness to obtain 381 mg of a colorless oily product with a yield of 91%.

LC-MS: 465.1 $(M+H)^+$.

14. Synthesis of Compound 1-18

Compound 1-17 (380 mg, 0.82 mmol) and p-toluenesulfonyl chloride (187 mg, 0.98 mmol) were dissolved in dichloromethane (20 mL), triethylamine (0.23 mL, 1.64 mmol) and 4-di Aminopyridine (10 mg, catalytic amount) were added, and the mixture was reacted at room temperature for 16 hours. The reaction solution was slowly poured into water and extracted with dichloromethane. The extract was washed with saturated saline solution, concentrated and evaporated to dryness, and purified by silica gel column chromatography (dchloromethane:methanol=30:1 elution) to obtain 263 mg of a brown-yellow foamy product with a yield of 52%.

LC-MS: 619.3 $(M+H)^+$.

15. Synthesis of Compound 1-19

Compounds 1-18 (260 mg, 0.42 mmol) and 1-3 (162 mg, 0.42 mmol) were dissolved in N,N-dimethylformamide (3 mL), and N,N-diisopropylethyl Amine (0.14 mL, 0.84 mol) was added, and the reaction was carried out at 50° C. for 48 hours. The reaction solution was slowly poured into water, extracted with ethyl acetate. The extract was washed with saturated saline solution, concentrated and evaporated to dryness, and purified by silica gel column chromatography (dchloromethane:methanol=10:1 elution) to obtain 192 mg of a brown-yellow foamy product with a yield of 55%.

LC-MS: 833.4 $(M+H)^+$.

16. Synthesis of Compound 1

Compound 1-19 (192 mg, 0.23 mmol) was dissolved in acetonitrile (30 mL), benzenesulfonic acid (109 mg, 0.69 mmol) was added, and the reaction was refluxed for 24 hours. The reaction solution was concentrated and evaporated to dryness, and purified by silica gel column chromatography (dichloromethane:methanol=8:1 elution) to obtain 50 mg of white foamy product with a yield of 29%.

LC-MS: 759.5 $(M+H)^+$.

$^1$HNMR (400 MHz, DMSO-d6) δ 10.97 (s, 1H), 8.23 (s, 1H), 7.71-7.58 (m, 3H), 7.49-7.39 (m, 2H), 7.21-7.11 (m,

6H), 7.06 (dd, J=8.4, 2.4 Hz, 1H), 5.07 (dd, J=13.2, 5.2 Hz, 1H), 4.65 (s, 1H), 4.40-4.22 (m, 2H), 4.19 (dd, J=5.6, 3.6 Hz, 2H), 3.77-3.69 (m, 2H), 3.47 (t, J=6.4 Hz, 2H), 3.17 (d, J=5.2 Hz, 1H), 3.08-2.82 (m, 3H), 2.70-2.51 (m, 2H), 2.42-2.28 (m, 3H), 2.22-2.13 (m, 2H), 2.12-1.92 (m, 3H), 1.92-1.84 (m, 2H), 1.58-1.50 (m, 2H), 1.49-1.42 (m, 2H).
Example 2 Synthesis of Compound 2
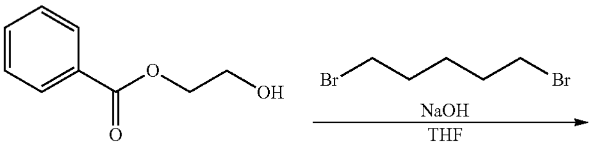
2-1
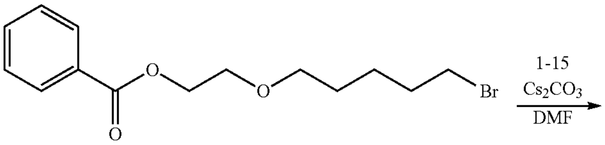
2-2
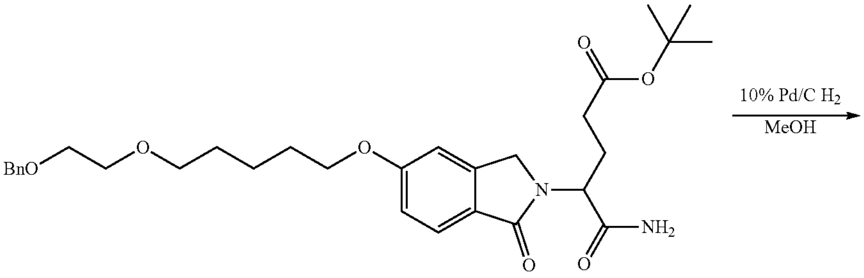
2-3
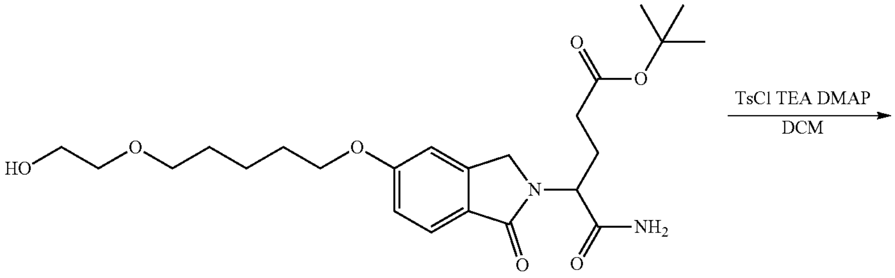
2-4
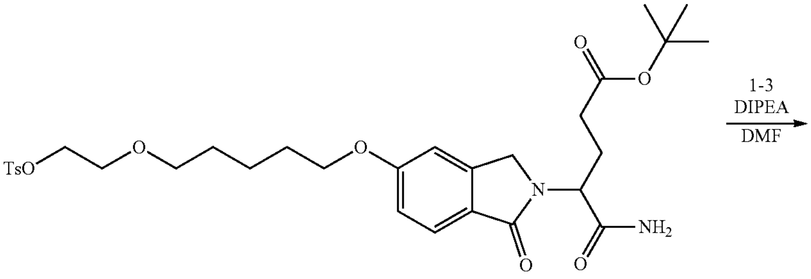
2-5

-continued

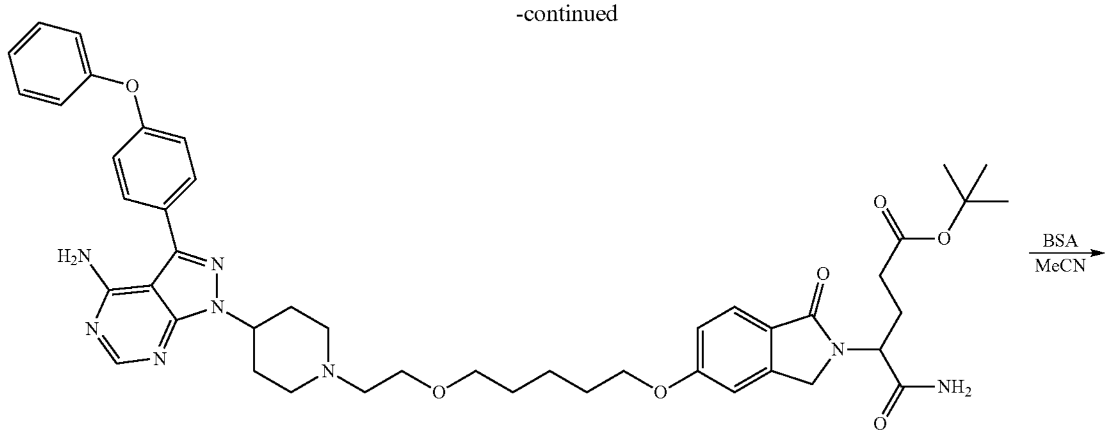

2-6

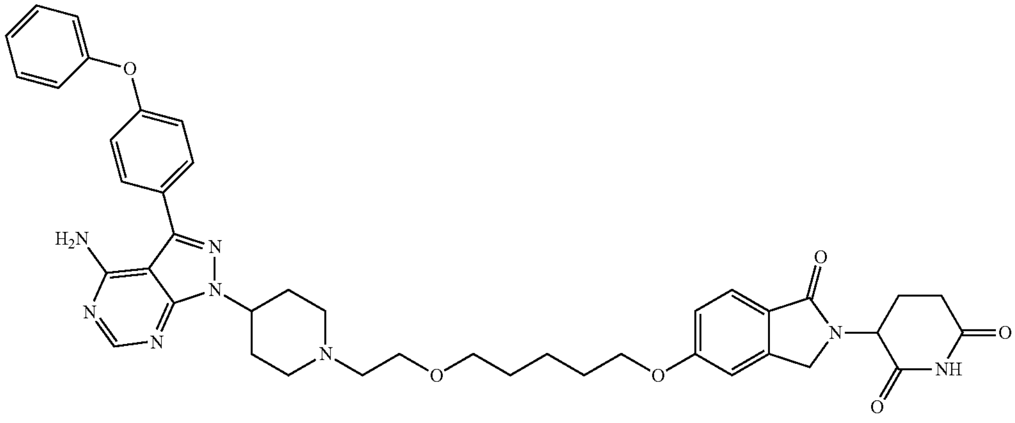

2

1. Synthesis of Compound 2-2

Compound 2-1 (30.0 g, 197 mmol) and 1,5-dibromopentane (44.9 g, 197 mmol) were dissolved in tetrahydrofuran solution (700 mL), and sodium hydroxide (23.6 g, 591 mmol) was added in batches, and the mixture was reacted at reflux for 16 hours. The reaction solution was cooled, slowly poured into ice water, and extracted with ethyl acetate. The extract was washed with saturated saline solution, concentrated and evaporated to dryness, and purified by silica gel column chromatography (petroleum ether:ethyl acetate=80:1 elution) to obtain 30.1 g of a light yellow oily liquid product with a yield of 51%.

LC-MS: 323.1 $(M+H)^+$.

21. Synthesis of Compound 2-3

Compound 1-15 (800 mg, 2.4 mmol) and cesium carbonate (1.5 g, 4.8 mmol) were dissolved in N,N-dimethylformamide (10 mL), and compound 2-2 (862 mg, 2.9 mol) was added, and the mixture was reacted at 50° C. for 16 hours. The reaction solution was slowly poured into water, extracted with ethyl acetate, the extract was washed with saturated saline solution, concentrated and evaporated to dryness, and purified by silica gel column chromatography (dichloromethane:methanol=50:1 elution) to obtain 612 mg of a brown-yellow foamy product with a yield of 46%.

LC-MS: 555.5 $(M+H)^+$.

12. Synthesis of Compound 2-4

Compound 2-3 (600 mg, 1.08 mmol) was dissolved in methanol (30 mL), added with 10% palladium on carbon (60 mg wet weight), and reacted at room temperature under hydrogen atmosphere for 16 hours. The reaction solution was filtered, concentrated and evaporated to dryness to obtain 462 mg of a colorless oily product with a yield of 92%.

LC-MS: 465.1 $(M+H)^+$.

13. Synthesis of Compound 2-5

Compound 2-4 (460 mg, 1.0 mmol) and p-toluenesulfonyl chloride (228 mg, 1.2 mmol) were dissolved in dichloromethane (20 mL), triethylamine (0.28 mL, 2.0 mmol) and 4-bis Aminopyridine (10 mg, catalytic amount) were added, and the mixture was reacted at room temperature for 16 hours. The reaction solution was slowly poured into water and extracted with dichloromethane. The extract was washed with saturated saline solution, concentrated and evaporated to dryness, and purified by silica gel column chromatography (dichloromethane:methanol=30:1 elution) to obtain 303 mg of a brown-yellow foamy product with a yield of 49%.

LC-MS: 619.0 $(M+H)^+$.

14. Synthesis of Compound 2-6

Compound 2-5 (300 mg, 0.48 mmol) and compound 1-3 (188 mg, 0.48 mmol) were dissolved in N,N-dimethylformamide (3 mL), and N,N-diisopropyl Ethylamine (0.17 mL, 0.97 mol) was added, and the reaction was carried out at 50° C. for 48 hours. The reaction solution was slowly poured into water, extracted with ethyl acetate, the extract was washed with saturated saline solution, concentrated and evaporated to dryness, and purified by silica gel column chromatography (dichloromethane:methanol=10:1 elution) to obtain 203 mg of a brown-yellow foamy product with a yield of 51%.

LC-MS: 833.5 $(M+H)^+$.

Synthesis of Compound 2

Compound 2-6 (203 mg, 0.24 mmol) was dissolved in acetonitrile (30 mL), benzenesulfonic acid (114 mg, 0.72 mmol) was added, and the reaction was refluxed for 24 hours. The reaction solution was concentrated and evaporated to dryness, and purified by silica gel column chromatography (dichloromethane:methanol=8:1 elution) to obtain 31 mg of a white foamy product with a yield of 17%.

LC-MS: 759.5 $(M+H)^+$.

$^1$HNMR (400 MHz, DMSO-d6) δ 10.97 (s, 1H), 8.23 (s, 1H), 7.72-7.63 (m, 2H), 7.59 (d, J=8.4 Hz, 1H), 7.49-7.40 (m, 2H), 7.22-7.09 (m, 6H), 7.03 (dd, J=8.4, 2.2 Hz, 1H), (dd, J=13.2, 5.2 Hz, 1H), 4.64 (s, 1H), 4.41-4.19 (m, 2H), 4.12-4.03 (m, 2H), 3.50 (t, J=6.0 Hz, 2H), 3.42 (t, J=6.4 Hz, 2H), 3.17 (d, J=5.2 Hz, 1H), 3.02 (d, J=6.4 Hz, 2H), 2.95-2.84 (m, 1H), 2.66-2.53 (m, 2H), 2.44-2.28 (m, 1H), 2.24-2.11 (m, 4H), 2.02-1.93 (m, 1H), 1.91-1.71 (m, 4H), 1.62-1.43 (m, 4H).

Example 3 Synthesis of Compound 3

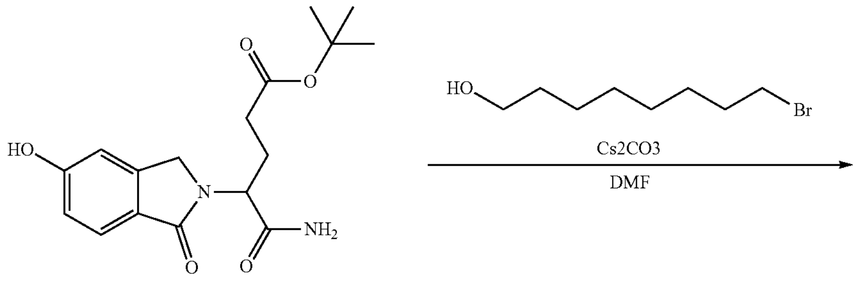

1-15

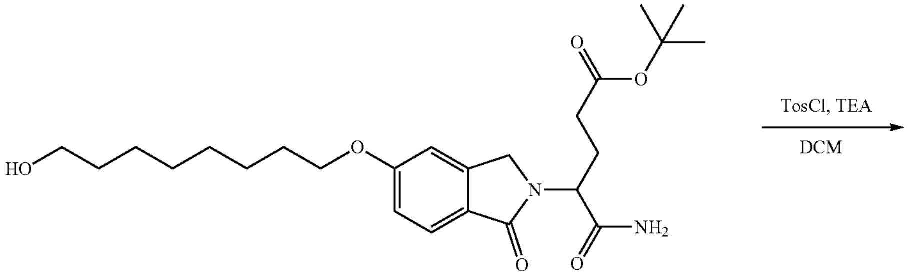

3-1

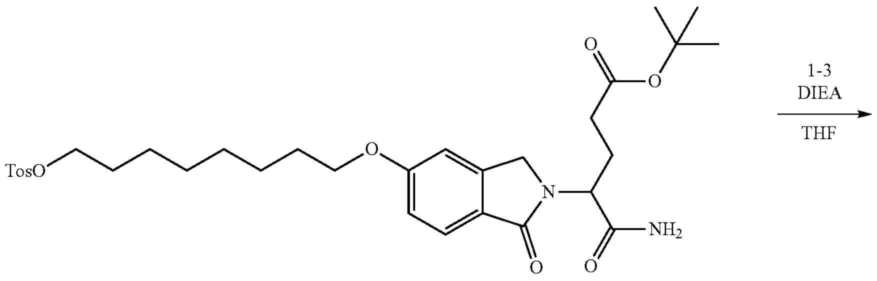

3-2

-continued

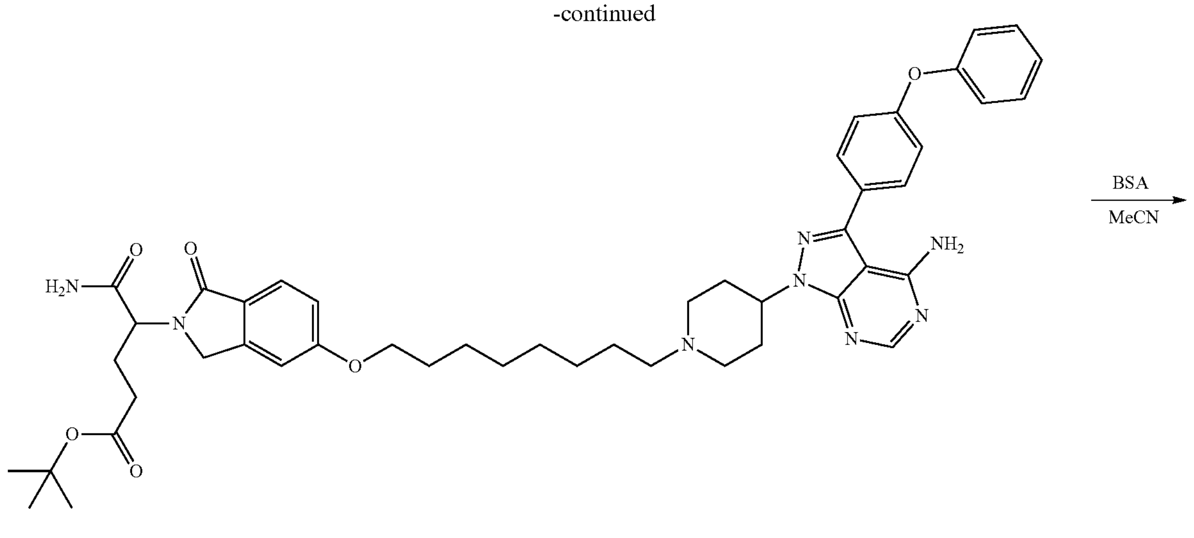

3-3

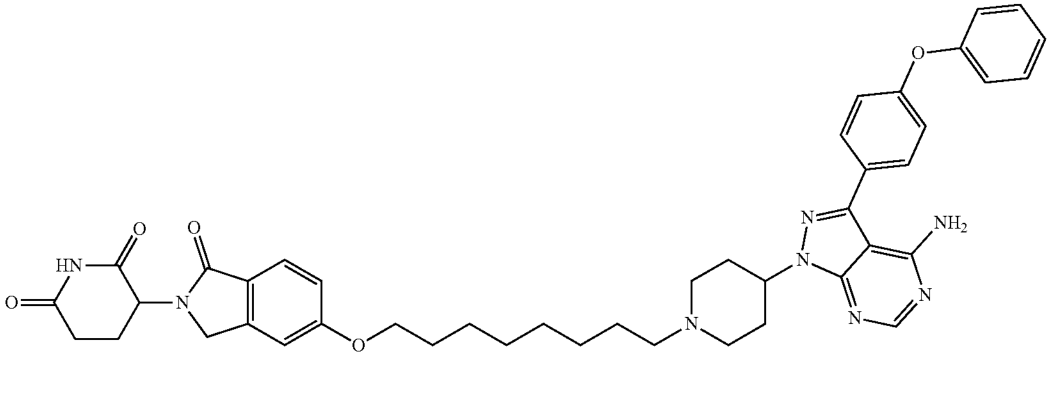

3

1. Synthesis of Compound 3-1

Compound 1-15 (800 mg, 2.4 mmol) and cesium carbonate (1.5 g, 4.8 mmol) were dissolved in N,N-dimethylformamide (10 mL), and 8-bromo-1-octanol (598 mg, 2.9 mol) was added, and the mixture was reacted at 50° C. for 16 hours. The reaction solution was slowly poured into water, extracted with ethyl acetate. The extract was washed with saturated saline solution, concentrated and evaporated to dryness, and purified by silica gel column chromatography (dichloromethane:methanol=50:1 elution) to obtain 508 mg of a brown-yellow foamy product with a yield of 46%.

LC-MS: 463.2 $(M+H)^+$.

2. Synthesis of Compound 3-2

Compound 3-1 (500 mg, 1.1 mmol) and p-toluenesulfonyl chloride (247 mg, 1.3 mmol) were dissolved in dichloromethane (20 mL), triethylamine (0.31 mL, 2.2 mmol) and 4-bis Aminopyridine (10 mg, catalytic amount) was added, and the mixture was reacted at room temperature for 16 hours. The reaction solution was slowly poured into water and extracted with dichloromethane. The extract was washed with saturated saline solution, concentrated and evaporated to dryness, and purified by silica gel column chromatography (dichloromethane:methanol=30:1 elution) to obtain 606 mg of a brown-yellow foamy product with a yield of 91%.

LC-MS: 617.4 $(M+H)^+$.

3. Synthesis of Compound 3-3

Compound 3-2 (300 mg, 0.48 mmol) and compound 1-3 (188 mg, 0.48 mmol) were dissolved in N,N-dimethylformamide (3 mL), and N,N-diisopropyl Ethylamine (0.17 mL, 0.97 mol) was added, and the reaction was carried out at 50° C. for 48 hours. The reaction solution was slowly poured into water, extracted with ethyl acetate. The extract was washed with saturated saline solution, concentrated and evaporated to dryness, and purified by silica gel column chromatography (dichloromethane:methanol=10:1 elution) to obtain 403 mg of a brown-yellow foamy product with a yield of 50%.

LC-MS: 831.5 $(M+H)^+$.

4. Synthesis of Compound 3

Compound 3-3 (400 mg, 0.48 mmol) was dissolved in acetonitrile (50 mL), benzenesulfonic acid (152 mg, 0.96 mmol) was added, and the reaction was refluxed for 24 hours. The reaction solution was concentrated and evaporated to dryness, and purified by silica gel column chromatography (dichloromethane:methanol=8:1 elution) to obtain 43 mg of a white foamy product with a yield of 12%.

LC-MS: 757.5 $(M+H)^+$.

$^1$H NMR (400 MHz, DMSO-d6) δ 10.98 (s, 1H), 8.24 (s, 1H), 7.73-7.57 (m, 4H), 7.47-7.40 (m, 2H), 7.23-7.10 (m, 7H), 7.04 (dd, J=8.4, 2.4 Hz, 1H), 5.07 (dd, J=13.2, 5.2 Hz, 1H), 4.67 (s, 1H), 4.41-4.21 (m, 2H), 4.15-4.01 (m, 3H), 3.17 (d, J=5.2 Hz, 2H), 3.10-2.84 (m, 3H), 2.69-2.52 (m, 2H), 2.48-2.26 (m, 4H), 2.26-2.04 (m, 4H), 2.03-1.83 (m, 4H), 1.79-1.70 (m, 2H), 1.50-1.40 (m, 4H).
Synthesis of Example 4 Compound 4
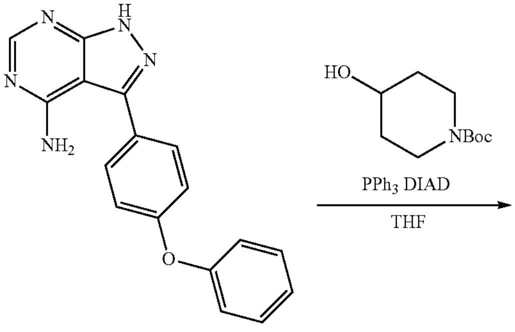
4-1
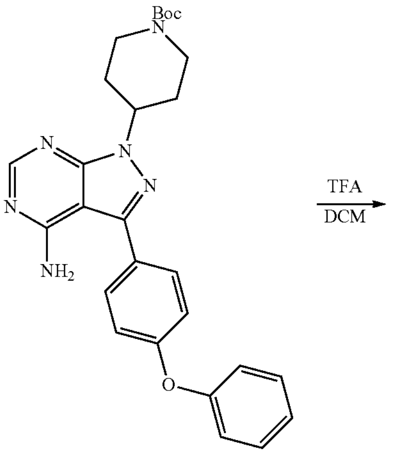
4-2
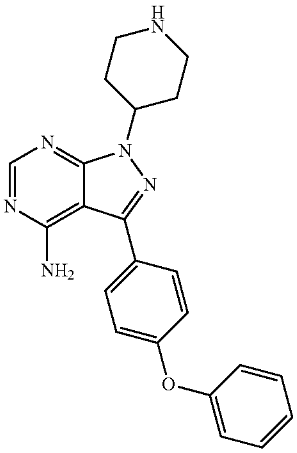
4-3
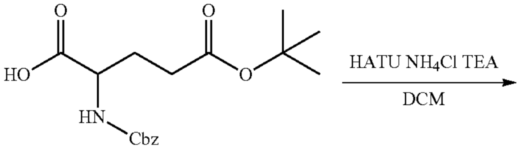
4-4
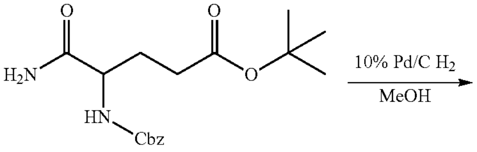
4-5
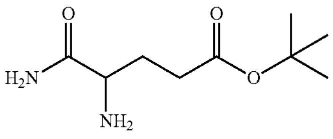
4-6
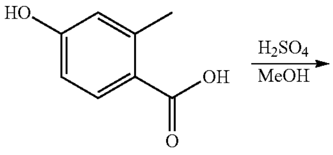
4-7
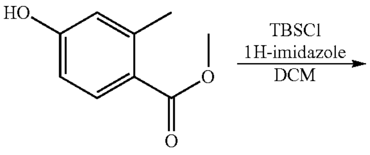
4-8
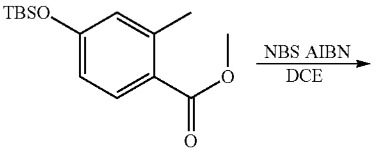
4-9

-continued
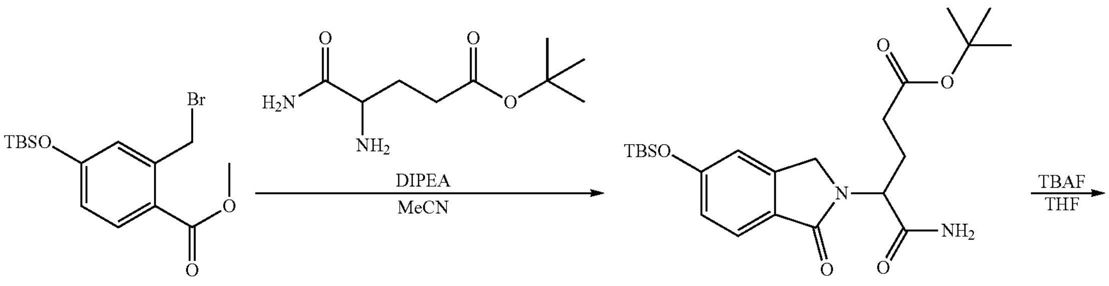
4-10 4-11
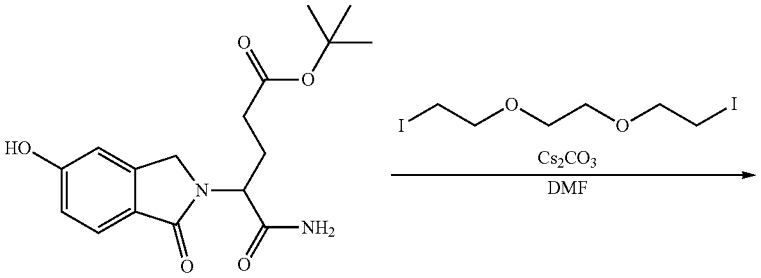
4-12
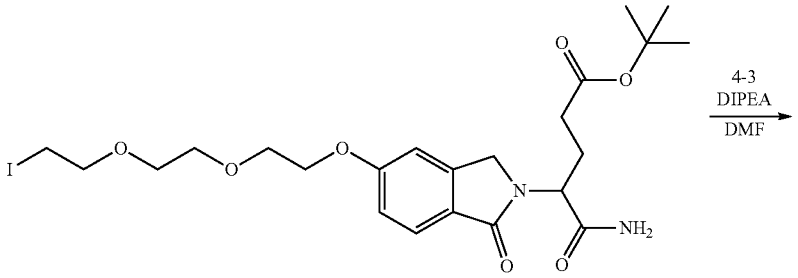
4-13
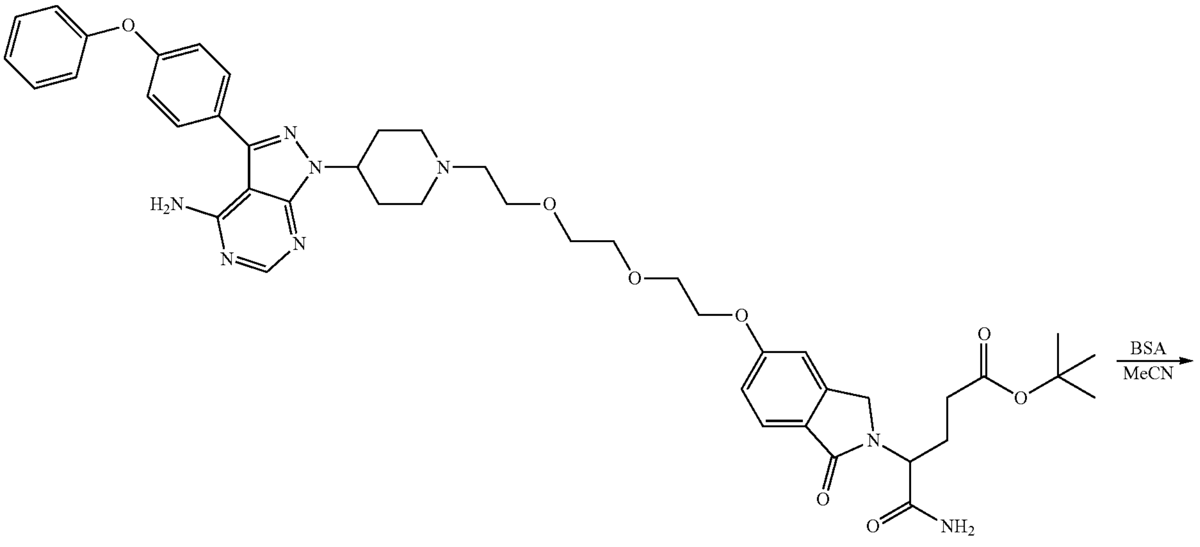
4-14

-continued

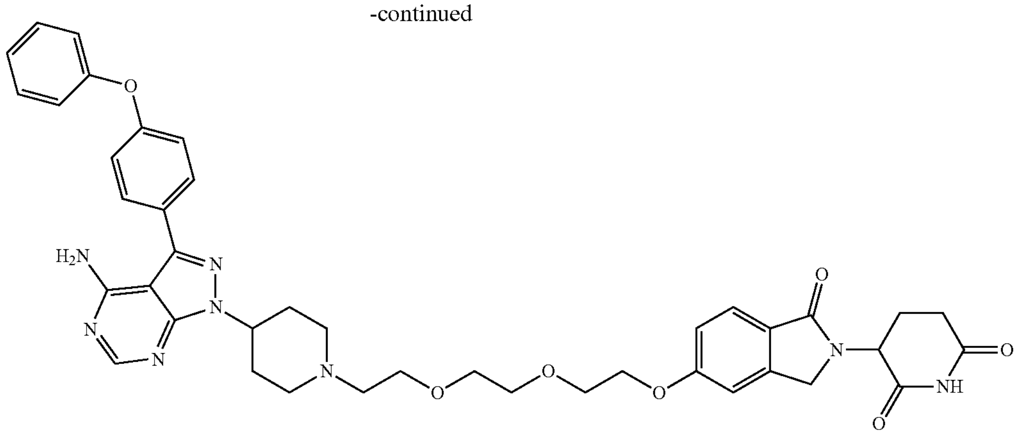

4

1. Synthesis of Compound 4-2

Compound 4-1 (3.0 g, 10 mmol), N-Boc-4-hydroxypiperidine (2.4 g, 12 mmol) and triphenylphosphine (3.9 g, 15 mmol) were dissolved in tetrahydrofuran (50 mL), and Diisopropyl azodicarboxylate (3.0 g, 15 mmol) was added dropwise, and the mixture was reacted at room temperature under nitrogen atmosphere for 16 hours. The reaction solution was diluted with an appropriate amount of ethyl acetate, washed with saturated saline solution, concentrated and evaporated to dryness, and purified by silica gel column chromatography (dichloromethane:methanol=50:1 elution) to obtain 3.0 g of a brownish-red foamy product with a yield of 78%.

LC-MS: 487.4 $(M+H)^+$

2. Synthesis of Compound 4-3

Compound 4-2 (3.0 g, 6 mmol) was dissolved in dichloromethane (30 mL), trifluoroacetic acid (3 mL) was slowly added dropwise, and the mixture was reacted at room temperature for 24 hours. The reaction solution was concentrated and evaporated to dryness, and purified by silica gel column chromatography (dichloromethane:methanol=30:1 elution) to obtain 2.2 g of a white foamy product with a yield of 93%.

LC-MS: 387.3 $(M+H)^+$ $^1$H NMR (400 MHz, DMSO-d6) δ 8.26 (s, 1H), 7.66 (d, J=8.0 Hz, 2H), 7.44 (t, J=7.6 Hz, 2H), 7.31-7.04 (m, 5H), 4.98 (prs, 1H), 3.40-3.33 (m, 2H), 3.13-2.99 (m, 2H), 2.36-2.18 (m, 2H), 2.13-1.96 (m, 2H).

3. Synthesis of Compound 4-5

Compound 4-4 (50.0 g, 148 mmol) and ammonium chloride (39.3 g, 742 mmol) were dissolved in dichloromethane (700 mL), and N,N,N,N-tetramethyl-O-(7-Azabenzotriazol-1-yl) urea hexafluorophosphate (68.0 g, 180 mmol) and triethylamine (100 mL, 0.75 mmol) was added, and the reaction was reacted at room temperature for 16 hours. The reaction solution was washed successively with dilute hydrochloric acid and saturated saline solution. The organic phase was concentrated and evaporated to dryness, and purified by silica gel column chromatography (dichloromethane:methanol=80:1 elution) to obtain 21.4 g of white solid product with a yield of 43%.

LC-MS: 359.2 $(M+Na)^+$

4. Synthesis of Compound 4-6

Compound 4-5 (21.4 g, 64 mmol) was dissolved in methanol (500 mL), added with 10% palladium-carbon (3.0 g wet weight), and reacted at room temperature under hydrogen atmosphere for 24 hours. The reaction solution was filtered, concentrated and evaporated to dryness to obtain 11.7 g of a light yellow oily product with a yield of 91%.

LC-MS: 203.1 $(M+H)^+$

Synthesis of Compound 4-8

Compound 4-7 (25.0 g, 164 mmol) was dissolved in methanol solution (150 mL), sulfuric acid (5 mL) was slowly added dropwise under ice-cooling, and the reaction was refluxed for 3 hours. The reaction solution was concentrated, slowly poured into water, and extracted with ethyl acetate. The extract was washed with saturated saline solution, concentrated and evaporated to dryness to obtain 20.5 g of a light red solid product with a yield of 75%.

LC-MS: 167.1 $(M+H)^+$ $^1$H NMR (400 MHz, DMSO-d6) δ 10.15 (s, 1H), 7.77 (d, J=9.2 Hz, 1H), 6.72-6.65 (m, 2H), 3.76 (s, 3H), 2.47 (s, 3H).

6. Synthesis of Compound 4-9

Compound 4-8 (20.0 g, 120 mmol) and imidazole (12.2 g, 180 mmol) were dissolved in dichloromethane (200 mL), and tert-butyldimethylsilyl chloride (21.6 g, 144 mmol) was added to react at room temperature 16 hours. The reaction solution was filtered, concentrated and evaporated to dryness, and purified by silica gel column chromatography (petroleum ether:ethyl acetate=50:1 elution) to obtain 19.8 g of a colorless oily product with a yield of 59%.

LC-MS: 281.2 $(M+H)^+$

7. Synthesis of Compound 4-10

Compound 4-9 (19.8 g, 70 mmol) and N-bromosuccinimide (13.8 g, 78 mmol) were dissolved in dichloroethane (200 mL), and azobisisobutyronitrile (1.1 g, 7 mmol) was added to react at 90° C. for 16 hours. The reaction solution was concentrated and purified by silica gel column chromatography (petroleum ether:ethyl acetate=100:1 elution) to obtain 30.1 g of a colorless oily product (purity 40%, containing a large amount of raw material and dibromide, difficult to separate).

LC-MS: 381.1 $(M+Na)^+$

8. Synthesis of Compound 4-11

Compounds 4-10 (24.0 g, 26.8 mmol, 40%) and 1-6 (6.8 g, 33.6 mmol) were dissolved in acetonitrile (200 mL), and N,N-diisopropylethylamine (12 mL, 68 mmol) was added to react at reflux for 16 hours. The reaction solution was concentrated and purified by silica gel column chromatography (petroleum ether:ethyl acetate=1:1 elution) to obtain 6.0 g of brown-yellow oily product with a yield of 40%.

LC-MS: 449.3 $(M+H)^+$

9. Synthesis of Compound 4-12

Compound 4-11 (6.0 g, 13.2 mmol) was dissolved in methanol (100 mL), and tetrabutylammonium fluoride (6.8 g, 26.4 mmol) was added to react at room temperature for 16 hours. The reaction solution was concentrated and purified by silica gel column chromatography (dichloromethane: methanol=20:1 elution) to obtain 3.7 g of a brown-yellow oily product with a yield of 83%.

LC-MS: 335.3 $(M+H)^+$ $^1$H NMR (400 MHz, DMSO-d6) δ 10.13 (s, 1H), 7.58-7.42 (m, 2H), 7.16 (s, 1H), 6.94 (d, J=2.0 Hz, 1H), 6.86 (dd, J=8.4, 2.0 Hz, 1H), 4.72-4.63 (m, 1H), 4.55-4.29 (m, 2H), 2.21-2.06 (m, 3H), 2.02-1.89 (m, 1H), 1.33 (s, 9H).

Synthesis of Compound 4-13

Compound 4-12 (1.2 g, 3.6 mmol) and cesium carbonate (2.4 g, 7.2 mmol) were dissolved in N,N-dimethylformamide (15 mL), and 1,2-bis(2-iodo Ethoxy)ethane (2.6 g, 7.2 mol) was added to react at room temperature for 2 hours. The reaction solution was slowly poured into water, extracted with ethyl acetate, the extract was washed with saturated saline solution, concentrated and evaporated to dryness, and purified by silica gel column chromatography (dichloromethane:methanol=50:1 elution) to obtain 520 mg of a brown-yellow foamy product with a yield of 25%.

LC-MS: 577.2 $(M+H)^+$

11. Synthesis of Compound 4-14

Compounds 4-13 (500 mg, 0.87 mmol) and 4-3 (335 mg, 0.87 mmol) were dissolved in N,N-dimethylformamide (3 mL), and triethylamine (0.6 mL, 4.34 mol) was added, and this reaction was carried out at 50° C. for 48 hours. The reaction solution was slowly poured into water, extracted with ethyl acetate. The extract was washed with saturated saline solution, concentrated and evaporated to dryness, and purified by silica gel column chromatography (dichloromethane:methanol=10:1 elution) to obtain 305 mg of a brown-yellow foamy product with a yield of 42%.

LC-MS: 835.3 $(M+H)^+$

12. Synthesis of Compound 4

Compound 4-14 (300 mg, 0.36 mmol) was dissolved in acetonitrile (30 mL), benzenesulfonic acid (114 mg, 0.72 mmol) was added, and the reaction was refluxed for 24 hours. The reaction solution was concentrated and evaporated to dryness, and purified by silica gel column chromatography (dichloromethane:methanol=8:1) to obtain 52 mg of white foamy product with a yield of 19%.

LC-MS: 761.3 $(M+H)^+$.

$^1$HNMR (400 MHz, DMSO-d6) δ 10.97 (s, 1H), 8.23 (s, 1H), 7.68-7.64 (m, 2H), 7.61 (d, J=8.4 Hz, 1H), 7.46-7.40 (m, 2H), 7.24-7.10 (m, 7H), 7.06 (dd, J=8.4, 2.4 Hz, 1H), 5.06 (dd, J=13.2, 5.2 Hz, 1H), 4.64 (s, 1H), 4.40-4.16 (m, 4H), 3.85-3.74 (m, 2H), 3.65-3.49 (m, 7H), 3.02 (s, 2H), 2.96-2.83 (m, 1H), 2.63-2.53 (m, 2H), 2.42-2.29 (m, 1H), 2.19 (s, 4H), 2.01-1.92 (m, 1H), 1.87 (s, 2H)

Example 5 Membrane Permeability and Efflux Tests of Compounds

Experimental Steps:

1) Caco-2 cells in the logarithmic growth phase were taken, digested and centrifuged and the cell concentration was adjusted to $4\times10^5$ cells/mL with MEM complete medium.
2) 0.5 mL of cell suspension was added to the apical side (AP side) and 1.5 mL MEM cell complete medium was added to the basal side (BL side) of the Transwell plate, respectively.
3) Culture in a cell constant temperature incubator, change the culture medium every two days, and change the medium every day after one week of culture.
4) After about 21 days, the resistance value of the formed continuous monolayer film is greater than 100 $\Omega\cdot cm^2$, and the transport experiment is carried out within 3-5 days.
5) The test compound solution was added to the AP side as the donor solution (Donor), and 1.5 mL of the receiver solution (Receiver) was added to the basal side (BL side). After the culture plate was placed in an incubator at 37° C. for 90 minutes, the AP side was separated from the BL side to terminate the reaction.
6) Donor or Receiver samples were diluted with 0.4% DMSO in HBSS, and then mixed with acetonitrile. The LC conditions were as follows: mobile phase A: $H_2O$—0.025% FA-1 mM $NH_4OAC$, B: MeOH-0.025% FA-1 mM $NH_4OAC$. Column: ACQUITY UPLC BEH_C18 (2.1×50 mM, 1.7 μm). Flow rate 0.60 mL/min. Gradient: 0.2 min 2% B, 0.6 min 98% B, 1.3 min 98% B, 1.31 min 2% B, 1.8 min stop.
7) Calculation formula:

Papp=(*VA*/(area×time))×([drug]receiver/([drug]donor)×dilution factor)

where VA is the volume in the receiving chamber, area is the surface area of the membrane, and time is the total transport time in seconds.

| Test Article | | $P_{app}(10^{-6}\ cm \cdot s^{-1})$ Sample-01 | Sample-02 | Mean | RSD | $P_{app}$(B-A)/$P_{app}$(A-B) |
|---|---|---|---|---|---|---|
| Compound 1 | A-B | 5.55 | 5.16 | 5.35 | 0.05 | 1.32 |
| | B-A | 7.18 | 6.99 | 7.09 | 0.02 | |
| Compound 2 | A-B | 2.37 | 2.26 | 2.32 | 0.03 | 1.18 |
| | B-A | 2.73 | 2.75 | 2.74 | 0.01 | |

-continued
| Test Article | | $P_{app}$($10^{-6}$ cm · $s^{-1}$) | | | | $P_{app}$(B-A)/ |
|---|---|---|---|---|---|---|
| | | Sample-01 | Sample-02 | Mean | RSD | $P_{app}$(A-B) |
| Compound 4 | A-B | 3.18 | 3.46 | 3.32 | 0.06 | 8.75 |
| | B-A | 25.07 | 33.04 | 29.05 | 0.19 | |
| Control | A-B | 1.07 | 1.04 | 1.05 | 0.02 | 32.99 |
| compound 1 | B-A | 30.17 | 39.38 | 34.77 | 0.19 | |
| Control | A-B | 1.02 | 1.00 | 1.01 | 0.01 | 18.13 |
| compound 2 | B-A | 18.10 | 18.65 | 18.37 | 0.02 | |
| Control | A-B | 2.14 | 2.16 | 2.15 | 0.01 | 15.86 |
| compound 3 | B-A | 33.54 | 34.75 | 34.15 | 0.02 | |
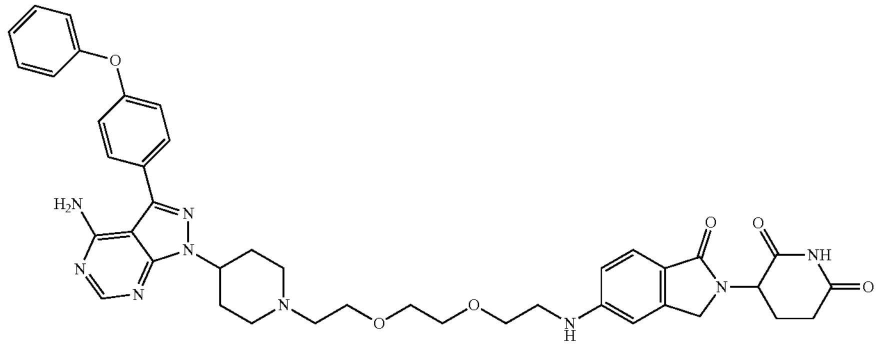
Control compound 1
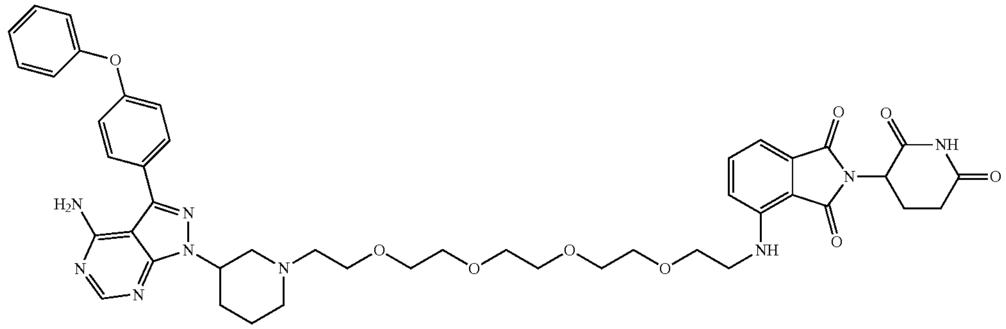
Control compound 2
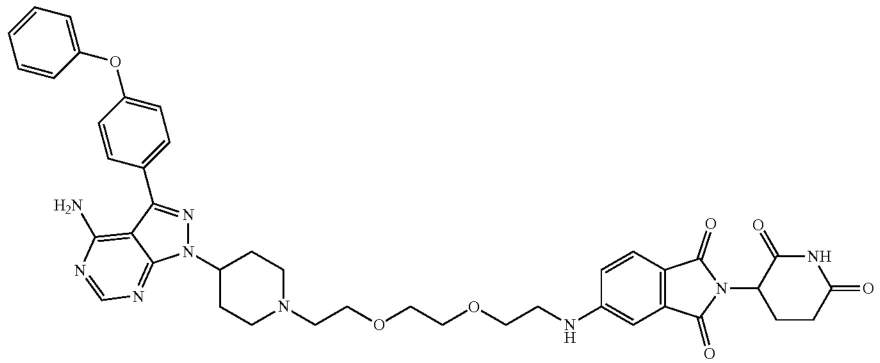
Control compound 3

Drug molecules cross the single cell layer or via the cell gap from the apical side (AP side) to the basolateral side (BL side) of the Caco-2 monolayer are A to B, and vice versa are B to A. The efflux ratio: Papp(B–A)/Papp(A–B). Experimental results showed that the compound of the invention had good permeability, was not a p-glycoprotein transport substrate, had no efflux phenomenon, and had good druggability.

Example 6 Western Blot Assay for Compound Degradation of BTK Protein

The Jeko-1 cell line was cultured in RPMI-1640 medium containing 20% fetal bovine serum in an incubator at 37° C., 5% $CO_2$, and saturated humidity. After the cells grew to the logarithmic growth phase, $5\times10^6$ cells per well were seeded in a 6-well culture plate, and a DMSO control group and a compound test group were set.

After 24 hours of drug treatment, the cells were collected, added pre-cooled cell lysate, and lysed on ice for 45 min. After the cells were completely lysed, they were centrifuged, and the supernatant was taken and stored in an ice bath. The protein concentration was determined by Bradford protein concentration assay kit (detergent compatible type), and protein samples were prepared. After the proteins were separated by SDS-PAGE gel electrophoresis, they were transferred to PVDF membranes by wet method and blocked with 5% BSA solution at room temperature for 1 h. Diluted rabbit anti-human BTK and GAPDH were added according to the experimental requirements, and incubated overnight at 4° C. After washing the membrane with TBST, horseradish peroxidase-labeled goat anti-rabbit IgG secondary antibody dilution was added and incubated at room temperature for 1 h. After washing the membrane with TBST, the ECL luminescent solution was added in the gel imager for development and imaging.

Image J software was used to perform grayscale analysis of each band, and GAPDH was used as an internal reference to calculate the half-degradation concentration (DC50) of the compound to degrade BTK protein.

The results show that the compound of the present invention has a strong activity of degrading BTK.

| Compound | Degradation of BTK activity DC50 (nM) |
|---|---|
| Compound 1 | 2.3 |
| Compound 2 | 1.5 |
| Compound 4 | 12.3 |

Example 7 Western Blot Assay for Compound Degradation of BTK-C481S Mutant Protein The TMD8 (BTK-C481S) mutant cell line was cultured in RPMI-1640 medium containing 20% fetal bovine serum in an incubator at 37° C., 5% $CO_2$, and saturated humidity. After the cells grew to the logarithmic growth phase, $5\times10^6$ cells per well were seeded in a 6-well culture plate, and a DMSO control group and a compound test group were set.

After 24 hours of drug treatment, the cells were collected, added pre-cooled cell lysate, and lysed on ice for 45 min. After the cells were completely lysed, they were centrifuged, and the supernatant was taken and stored in an ice bath. The protein concentration was determined by Bradford protein concentration assay kit (detergent compatible type), and protein samples were prepared. After the proteins were separated by SDS-PAGE gel electrophoresis, they were transferred to PVDF membranes by wet method and blocked with 5% BSA solution at room temperature for 1 h. Diluted rabbit anti-human BTK and GAPDH were added according to the experimental requirements, and incubated overnight at 4° C. After washing the membrane with TBST, horseradish peroxidase-labeled goat anti-rabbit IgG secondary antibody dilution was added and incubated at room temperature for 1 h. After washing the membrane with TBST, the ECL luminescent solution was added in the gel imager for development and imaging.

Image J software was used to perform gray scale analysis of each band, and GAPDH was used as an internal reference to calculate the half-degradation concentration (DC50) of the compound to degrade BTK protein.

The results show that the compound of the present invention has strong activity of degrading BTK-C481S.

| Compound | Degradation BTK-C481S activity DC50 (nM) |
|---|---|
| Compound 1 | 9.9 |
| Compound 2 | 3.1 |
| Compound 4 | 17 |

Example 8 Proliferation Inhibition of TMD8(BTK-C481S) Mutant Cells by the Compound Cell culture: TMD8 (BTK-C481S) mutant cell line (human lymphoma cells) was cultured in RPMI-1640 complete medium containing 10% fetal bovine serum and 1% penicillin-streptomycin in an incubator at 37° C., 5% $CO_2$ and saturated humidity conditions.

Cell plating: TMD8 (BTK-C481S) mutant cells in the logarithmic growth phase were taken, centrifuged, and an appropriate amount of complete medium was added to obtain a single-cell suspension. Cell counting was carried out with a hemocytometer, and a cell suspension of $1.5\times10^5$ cells/mL was prepared. 100 μL of cell suspension per well was inoculated in a 96-well culture plate, and cultured in a $CO_2$ cell incubator for 24 hours.

Cell administration: The compound to be tested in the Example was prepared as a 2.5 μM master mix, and 25 μL of the Example compound was added to each well. The plates were shaken well, placed in a $CO_2$ cell incubator, and continued to incubate for 72h.

CCK-8 detection: 72 hours after administration, 10% CCK-8 solution was added to each well. The plates were placed in a $CO_2$ cell incubator, and incubated for 1-4 hours. The absorbance of each well was measured at 450 nm using a microplate reader.

Calculation of cell proliferation inhibition rate:

$$\text{Cell proliferation inhibition rate } (\%)=[(Ac-As)/(Ac-Ab)]\times100\%$$

As: Absorbance of experimental well (including cells, medium, CCK-8 solution and drug solution)

Ac: Absorbance of control well (containing cells, medium, CCK-8 solution, without drug)

Ab: Absorbance of blank well (containing culture medium, CCK-8 solution, excluding cells and drugs)

The results show that the compound of the present invention has strong proliferation inhibitory activity on TMD8 (BTK-C481S) mutant cells.

| Compound | $IC_{50}$(nM) |
|---|---|
| Ibrutinib | 125 |
| Compound 1 | 7.1 |
| Compound 2 | 17.7 |

Example 9 Anti-Tumor Effect of the Compound in Mouse OCI-LY10 Tumor Model

OCI-LY10 cells were cultured in RPMI-1640 medium containing 10% fetal bovine serum (FBS). Cells were cultured at 37° C. in a 5% $CO_2$ incubator.

Cell inoculation method to establish tumor SCID mouse subcutaneous transplantation model: tumor cells in logarithmic growth phase were collected, counted and resuspended in RPMI-1640 medium. Matrigel was added at 1:1, and the concentration of cell suspension was adjusted to $4\times10^7$ cells/ml. Inoculate tumor cells subcutaneously on the right back of SCID mice with a 1 ml syringe, $4\times10^6$ cells/0.1 ml/mouse When the average volume of animal tumors is about 140 $mm^3$, animals with too large tumor, too small tumor, or have irregular tumor shapes were eliminated. The tumor-bearing mice with tumor volumes ranging from 101.34 to 209.86 mm 3 were selected, and were divided into groups by random block method, respectively as model group, compound group (oral 100 mg/kg, twice a day), 7 mice in each group. The day of grouping was Day 0, and administration was started according to the body weight of the animals.

After 14 days of administration, the tumor volume was measured, and the tumor inhibition rate was calculated, and the calculation formula was as follows:

Tumor inhibition rate=[1−(Day14 tumor volume−Day0 administration tumor volume)/Day0 administration tumor volume]*100%

The results showed that the compounds of the present invention had a strong in vivo antitumor effect, causing almost complete tumor regression.

| Compound | Tumor inhibition rate |
|---|---|
| Compound 1 | 175% |
| Compound 2 | 189% |

All publications mentioned herein are incorporated by reference as if each individual document is cited as a reference, as in the present application. It should also be understood that, after reading the above teachings of the present invention, those skilled in the art can make various changes or modifications, equivalents of which falls in the scope of claims as defined in the appended claims.

What is claimed is:

1. A compound, or a pharmaceutically acceptable salt thereof, or a deuterated compound thereof, wherein the compound is selected from the group consisting of:

| No. | Structure |
|---|---|
| 1 | 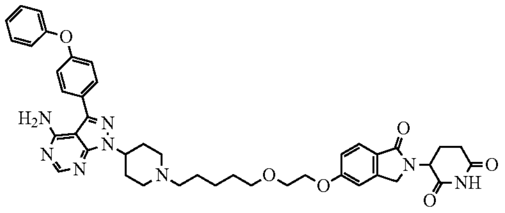 [SMILES: Nc1ncnc2c1c(-c1ccc(Oc3ccccc3)cc1)nn2C1CCN(CCCCCOCCOc2ccc3c(c2)CN(C2CCC(=O)NC2=O)C3=O)CC1] |
| 2 | 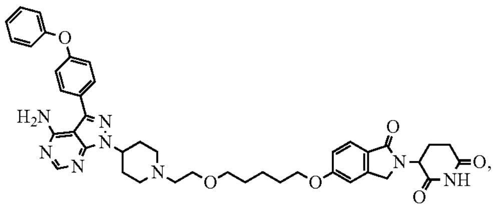 [SMILES: Nc1ncnc2c1c(-c1ccc(Oc3ccccc3)cc1)nn2C1CCN(CCOCCCCCOc2ccc3c(c2)CN(C2CCC(=O)NC2=O)C3=O)CC1] |
| | and |
| 3 | 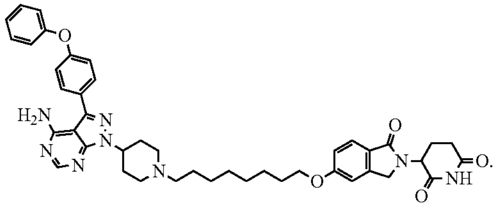 [SMILES: Nc1ncnc2c1c(-c1ccc(Oc3ccccc3)cc1)nn2C1CCN(CCCCCCCCOc2ccc3c(c2)CN(C2CCC(=O)NC2=O)C3=O)CC1] |

2. The compound of claim 1, or the pharmaceutically acceptable salt thereof, or the deuterated compound thereof, wherein the compound is:

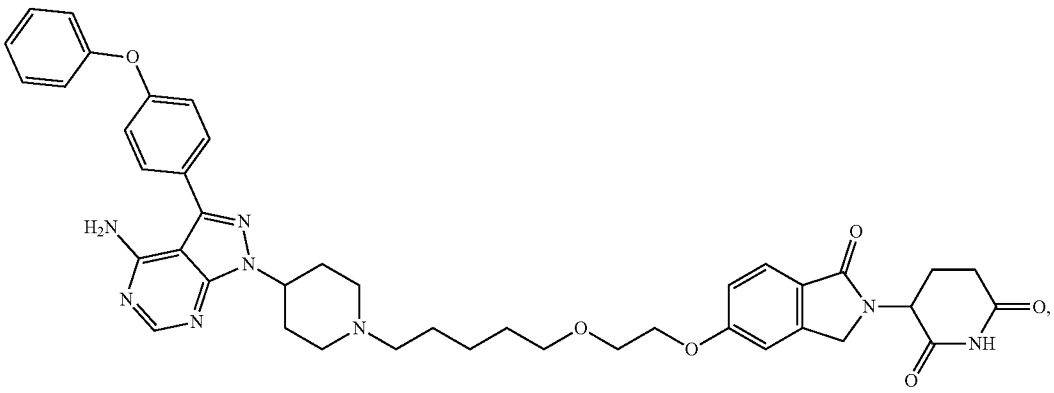 or

-continued

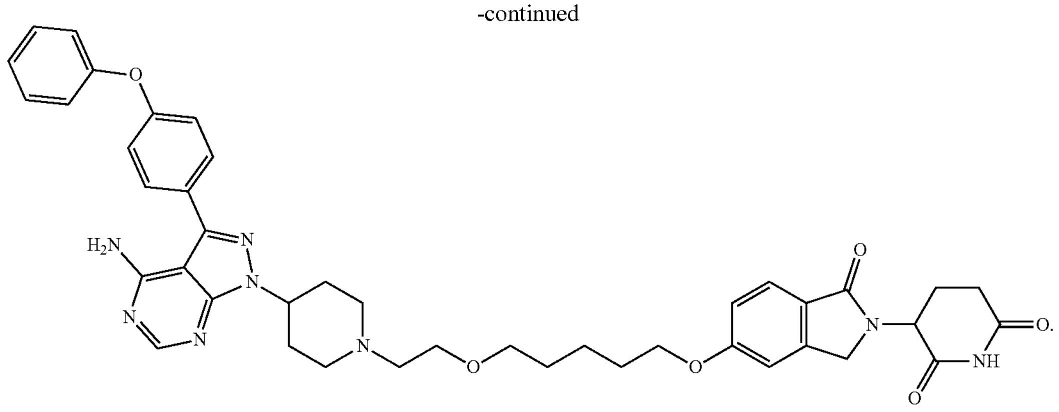

3. A pharmaceutical composition, wherein the composition comprises the compound according to claim 1, or the pharmaceutically acceptable salt thereof, or the deuterated compound thereof, and a pharmaceutically acceptable carrier.

4. The pharmaceutical composition of claim 3, wherein the pharmaceutical composition further comprises one or more antineoplastic agents.

5. A method for treating a lymphoma, comprising: administering to a subject in need thereof a therapeutically effective amount of the compound according to claim 1, or the pharmaceutically acceptable salt thereof, or the deuterated compound thereof; or administering to a subject in need thereof a therapeutically effective amount of a pharmaceutical composition wherein the pharmaceutical composition comprises the compound according to claim 1, or the pharmaceutically acceptable salt thereof, or the deuterated compound thereof, and a pharmaceutically acceptable carrier.

6. The method of claim 5, wherein the lymphoma is non-Hodgkin's lymphoma (NHL) or B cell lymphoma.

7. A method for inhibiting or degrading Bruton's tyrosine protein kinase (Btk) activity, comprising administering to a subject in need thereof an inhibitory effective amount of the compound according to claim 1, or the pharmaceutically acceptable salt thereof, or the deuterated compound thereof, or administering to a subject in need thereof an inhibitory effective amount of a pharmaceutical composition wherein the pharmaceutical composition comprises the compound according to claim 1, or the pharmaceutically acceptable salt thereof, or the deuterated compound thereof, and a pharmaceutically acceptable carrier.

* * * * *